(12) United States Patent
Abatangelo et al.

(10) Patent No.: US 6,482,231 B1
(45) Date of Patent: *Nov. 19, 2002

(54) BIOLOGICAL MATERIAL FOR THE REPAIR OF CONNECTIVE TISSUE DEFECTS COMPRISING MESENCHYMAL STEM CELLS AND HYALURONIC ACID DERIVATIVE

(76) Inventors: Giovanni Abatangelo, Via Pelosa 32, 35030 Saccolongo (Prov. of Padova) (IT); Lanfranco Callegaro, Via Monte Grappa 6, 35016 Thiene (Prov. of Vicenza) (IT); Randell G. Young, 8418 West Grove Rd., Ellicott City, MD (US) 21043; Josephine Mary Murphy, 2510 Pickwick Rd., Baltimore, MD (US) 21207; David Jordan Fink, 303 Wendover Rd., Baltimore, MD (US) 21218; Scott Philip Bruder, 3698 Ashley Way, Owings Mills, MD (US) 21117; Francis Peter Barry, 2510 Pickwick Rd., Baltimore, MD (US) 21207; Sudhakar Kadiyala, 1531 Lancaster St., Baltimore, MD (US) 21231; Arnold I. Caplan, 1300 Oakridge Dr., Cleveland Heights, OH (US) 44121; Roland Moskowitz, 2846 Montgomery Rd., Shaker Heights, OH (US) 44122; Jung U. Yoo, 16301 Shaker Blvd., Shaker Heights, OH (US) 44122; Luis A. Solchaga, 2260 Barrington Rd., University Heights, OH (US) 44118

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/602,033

(22) Filed: Jun. 23, 2000

Related U.S. Application Data

(63) Continuation of application No. 09/039,200, filed on Mar. 13, 1998, now abandoned, which is a continuation-in-part of application No. 09/041,287, filed on Mar. 12, 1998, said application No. 09/039,200, filed on Mar. 13, 1998, is a continuation-in-part of application No. PCT/EP96/05093, filed on Nov. 19, 1996.

(30) Foreign Application Priority Data

Nov. 20, 1995 (IT) ............................. PD95A0225

(51) Int. Cl.$^7$ ................................................. A61F 2/02
(52) U.S. Cl. ...................................................... 623/11.11
(58) Field of Search ................................. 623/919, 920, 623/23.51, 23.72; 435/325; 424/422, 423, 484, 499

(56) References Cited

U.S. PATENT DOCUMENTS

| | | | | |
|---|---|---|---|---|
| 5,032,508 A | * | 7/1991 | Naughton et al. | ............ 435/32 |
| 5,041,138 A | * | 8/1991 | Vacanti et al. | ............ 424/422 |
| 5,133,755 A | * | 7/1992 | Brekke | ............ 623/23.51 |
| 5,206,023 A | * | 4/1993 | Hunziker | ............ 424/423 |
| 5,226,914 A | * | 7/1993 | Caplan et al. | ............ 435/325 |
| 5,458,739 A | * | 10/1995 | Slivka et al. | ............ 202/153 |
| 5,520,916 A | * | 5/1996 | Dorigatti et al. | ............ 424/402 |
| 5,652,347 A | * | 7/1997 | Pouyani et al. | ............ 536/18.5 |
| 5,939,323 A | * | 8/1999 | Valentini et al. | ............ 435/395 |

* cited by examiner

Primary Examiner—David J. Isabella
(74) Attorney, Agent, or Firm—Hedman & Costigan, P.C.

(57) ABSTRACT

A biological material for the repair of connective tissue cells comprising:
  a) a cell preparation enriched in mesenchymal stem cells,
  b) three-dimensional extracellular matrix comprising a hyaluronic acid derivative.

The use of said biological material, optionally combined with therapeutically acceptable excipients and/or diluents and optionally in association with therapeutically effective ingredients in the repair of connective tissue cells.

16 Claims, 34 Drawing Sheets

BIOLOGICAL MATERIAL FOR THE REPAIR OF CONNECTIVE TISSUE DEFECTS COMPRISING MESENCHYMAL STEM CELLS AND HYALURONIC ACID DERIVATIVE

The present application is a continuation of Ser. No. 09/039,200, filed Mar. 13, 1998, now abandoned, which was a continuation-in-part of Ser. No. 09/041,287, filed Mar. 12, 1998, and said Ser. No. 09/039,200, filed Mar. 13, 1998 is also a continuation-in-part of and claims priority to International Application No. PCT/EP96/05093, filed Nov. 19, 1996 and Italian Application Ser. No. PD95A000225 filed Nov. 20, 1995.

FIELD OF THE INVENTION

The present invention relates to a biological material comprising mesenchymal stem cells and a three-dimensional matrix comprising a hyaluronic acid derivative thereof and the use of said biological material optionally in association with therapeutically effective ingredients and/or pharmaceutically acceptable excipients and/or diluents for the repair of connective tissue defects.

BACKGROUND OF THE INVENTION

The loss of connective tissue and in particular cutaneous material due to various causes, traumatic, or metabolic, for example, can sometimes prove to be very slow healing.

This can be due to metabolic or local circulatory causes, the patient's poor state of health or to the size of the wound, as in the case of extensive burns. The ineffectiveness of pharmacological therapy has led physicians to resort to reconstructive surgery, using connective tissue graft, such as skin graft, from the same patients whenever possible. An important breakthrough in the treatment of such lesions is the use of techniques for in vitro cell cultures.

J. Rheinwald and H. Green (Cell, 6,1975, 331–344) were the first to isolate keratinocytes which could be successfully used to cover skin lesions in clinical practice (G. G. Gallico et al., N. Engl., J Med., 311, (1984), 488–451). This innovative technique proved to have its limits, however, the most serious being the extreme fragility of the epithelial layer and the very low take rate. To overcome these limitations, dermal derivatives have been reconstructed on which keratynocytes can be grown. Yannas et al (Science, 215 (1982), 174–176) used a mixture of collagen and glycosaminoglycans to obtain a porous reabsorbable material to serve as a skin substitute on lesions characterised by the loss of cutaneous substance.

S. Boyce and J. Hansbrough (Surgery, 103 (1988), 421–431) described the use of layers of collagen and glycosaminoglycans as supports on which to grow keratinocytes for subsequent graft.

Another system for the preparation of dermal substitutes is represented by fibroblast cultures on biocompatible three-dimensional matrices based on synthetic or semisynthetic polymers. It is possible to seed and grow fibroblasts on these structures, thus enabling the production of an extracellular matrix similar to that of natural connective tissue.

Some well-known examples of dermal substitutes are:
1. Dermagraft, developed by Advanced Tissue Science (California), in which human fibroblasts are seeded and cultivated on a matrix formed by polylactic, polyglycolic or polygalactoside acid. These fibroblast-populated matrices are subsequently seeded with keratinocytes, to enhance their more "physiological" growth;
2. Graft-skin by Organogenesis Inc. (Boston USA) composed of a collagen substrate on which heterologous human fibroblasts are seeded;
3. Alloderm, produced by Life Cell Corp.(Texas USA) constituted by human or pig dermis, left intact and stored at a low temperature. Before use it can be seeded with autologous fibroblasts and keratinocytes and then used for grafting.

Although these products represent good biological supports for in vitro cultures, their in vivo application is somewhat limited, due to immunological reactions against their non autologous components, as well as to the risk of viral contamination.

Another problem involved in the preparation of connective tissue substitutes is represented by the supply of connective tissue cells to seed onto the biocompatible matrices. Indeed it is not always easy to isolate connective tissue cells, especially in the case of elderly or severely weakened subjects. One solution to this problem is offered by mesenchymal stem cells. Mesenchymal stem cells (MSC) are the formative pluripotential blast cells found inter alia in bone marrow, blood dermis and periosteum that are capable of differentiating into any of the specific types of mesenchymal stem or connective tissue cells such as adipose, osseous, cartilaginous, elastic, and fibrous connective tissues, depending upon various influences from bioactive factors such as cytokines. Although these cells are normally present at very low frequencies in bone marrow, a process has been discovered for isolating, plurifying and greatly replicating these cells in cultures, as disclosed by Caplan and Haynesworth in U.S. Pat. No. 5,486,359.

In order to isolate human MSC, it is necessary to isolate rare pluripotent mesenchymal stem cells from other cells in the bone marrow or other MSC source. Bone marrow cells may be obtained from iliac crest, femora, tibiae, spine, rib or other medullary spaces. Other sources of human mesenchymal stem cells include embryonic yolk sac, placenta, umbilical cord, fetal and adolescent skin, blood and other mesenchymal stem cell tissues.

Isolated human mesenchymal stem cell compositions serve as the progenitors for various mesenchymal cell lineages. Isolated mesenchymal stem cell populations have the ability to expand in culture without differentiating and have the ability to differentiate into specific mesenchymal lineages when either induced in vitro or placed in vivo at the place of the damaged tissue.

Hyaluronic acid or hyaluronan is a linear polyanionic polysaccharide, a member of the family known as glycosaminoglycans. It is present in most vertebrate connective tissue at relatively high concentrations (up to 10 mg/ml) (Kvam, K. C. Granese, D. Flaibani, A., Zanetti, F. and Paoletti, S (1993) Anal. Biochem. 211, 44–49).

The basic structural unit is a disaccharide consisting of D-glucuronic acid (GlcA) in $b_{1-3}$ linkage to N-acetyl-D-glucosamine (GlcNAc) and the disaccharides are linked together in a $b_{1-4}$ linkage. The molecular weight may be as high as $1 \times 10^7$ Da, so that in its highly hydrated form, hyaluronan shows unique properties of viscoelasticity and plasticity.

In cartilage, hyaluronic acid plays a central role in the assembly of the macromolecular components that constitute the extracellular matrix (Hardingham T. E. and Muir, H (1972) Biochim. Biophys. Acta 279,401–405) It binds with high specificity and affinity to aggregan and link protein (Neame, P. J, and Barry F. P. (1994) Experientia 49, 393–402.). A single hyaluronic acid chain may form a central "filament" that binds a large number of aggregan molecules, forming a supermolecular complex that immobilises water and leads to a highly hydrated gel-like structure (Morgelin, M., Paulson, M., and Angel J., (1990) Biochem. Soc. Trans. 18, 204–207). In addition hyaluronic acid binds with high affinity to the chondrocyte receptor CD44 (Knudson, C. B. (1993) J. Cell Biochem. 120, 825–834). Hyaluronic acid is present in the vitreous of the eye and in the synovial fluid in joint cavities. It is used in surgical procedures involving the anterior portion of the eye, such as corneal transplants and the removal and replacement of a cataractous lens.(Balasz E. A. (1991) "Cosmetic and pharmaceutical Applications of polymers" Gebelein C. G. et al ed.) Plenum Press New York). It is also used in the therapy of arthritis where injection of hyaluronic acid into the joint space may restore the rheological properties of the synovial fluid.(Larsen, N. E., Lombard, K. M., Parent, E. G. and Balasz, E. A., (1992) J. Orthop. Res. 10, 23–32).

Hyaluronic acid can be chemically treated to alter its biophysical and biological properties. For instance, it can be treated with formaldehyde or vinyl sulfone to give rise to cross-linked gels which have rheological properties different from the native molecule. (Abatangelo, G., Brun P., and Cortivo R.(1994) "Novel biomaterials based on hyaluronic acid and its derivatives"(Williams D. F. Ed) Fidia Advanced Biopolymers S.r.l. Italy). In addition, various hyaluronic acid derivatives are known from literature, for example the hyaluronic acid esters with different aromatic aliphatic and/or araliphatic alcohols like those disclosed in U.S. Pat. No. 4,851,521, with altered rheological properties if compared with the hyaluronic acid (Benedetti L., Bellini, D., Renier, D and O'Reagan M, (1994) in "Novel biomaterials based on hyaluronic acid and its derivatives" (Williams D. F. Ed) Fidia Advanced Biopolymers s.r.l. Italy). The water solubility of hyaluronic acid is dramatically reduced in the above mentioned hyaluronic acid esters, thus resulting in a major increase in the biological performance of this material (the previous reference).

Hyaluronic acid esters are known to be used in skin grafts thanks to their highly biocompatible and biodegradable materials. (Benedetti et al., Biomaterials, 14 (1993) 1154–1160; R. Cortivo et al., Biomaterials, 12 (1991) 727–730) and their lack of immunoreactivity.

Other hyaluronic acid derivatives such as the crosslinked hyaluronic acid polymers (ACP), namely the internal esters between the carboxylic function of a disaccharide unit of hyaluronic acid with a hydroxy function of another disaccharide unit of the same hyaluronic acid molecule or of a different hyaluronic acid molecule, are disclosed in U.S. Pat. No. 5,676,964. Both these hyaluronic acid derivatives can be in different physical forms Such as in the form of nonwoven tissue, sponges, gels etc.

SUMMARY OF THE INVENTION

In one aspect the present invention relates to a biological material comprising the following components:

a) a cell preparation enriched in mesenchymal stem cells, b) a three-dimensional matrix containing a hyaluronic acid derivative.

In another aspect the present invention relates to a composition comprising the above biologic material in combination with pharmaceutically acceptable excipients and/or diluents possibly associated with therapeutically active ingredients, for the repair of connective tissue defects.

In an other aspect the present invention relates to implants consisting essentially of said biological material, for the repair of connective tissue defects In another aspect, the present invention provides a therapeutic method for de novo formation of connective tissue in vivo by introducing into a site for de novo connective tissue formation in an individual in need thereof a therapeutically effective amount of the above mentioned composition comprising the biological material according to the present invention.

Finally, the present invention relates also to a surgical method for de novo formation of connective tissue in vivo by introducing into a site for de novo connective tissue formation in an individual in need thereof the above mentioned implants consisting essentially of the biological material, according to the present invention.

7C) 1.0% and grown in culture for 11 days. Sections were stained with Toluidine blue.

Figure 7A:
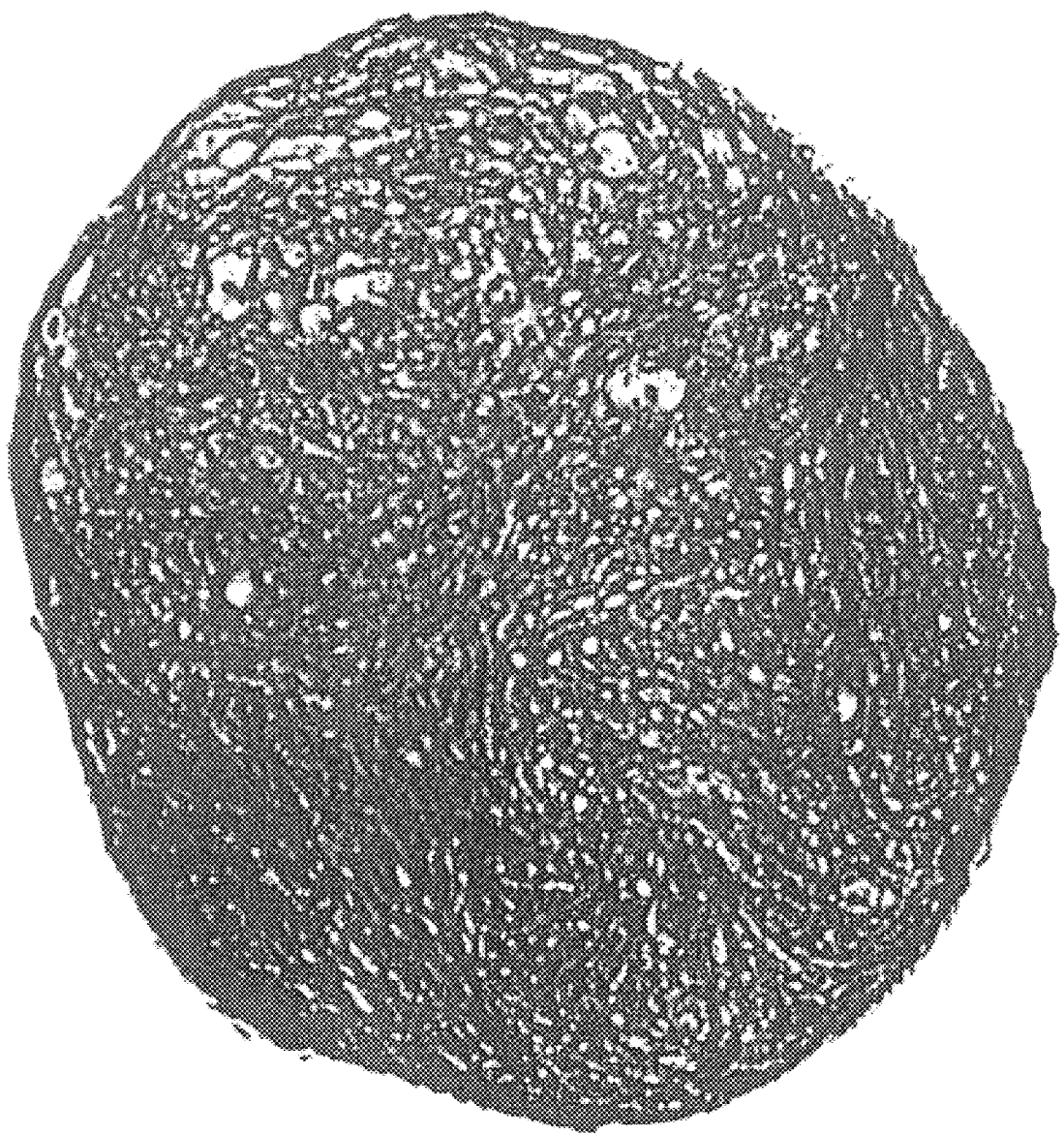
FIGS. 7A, 7B, and 7C MSCs were seemed onto ACP gel at concentrations of (FIG. 7A) 0.25, (FIG. 7B) 0.5 and (FIG.
Figure 7B:
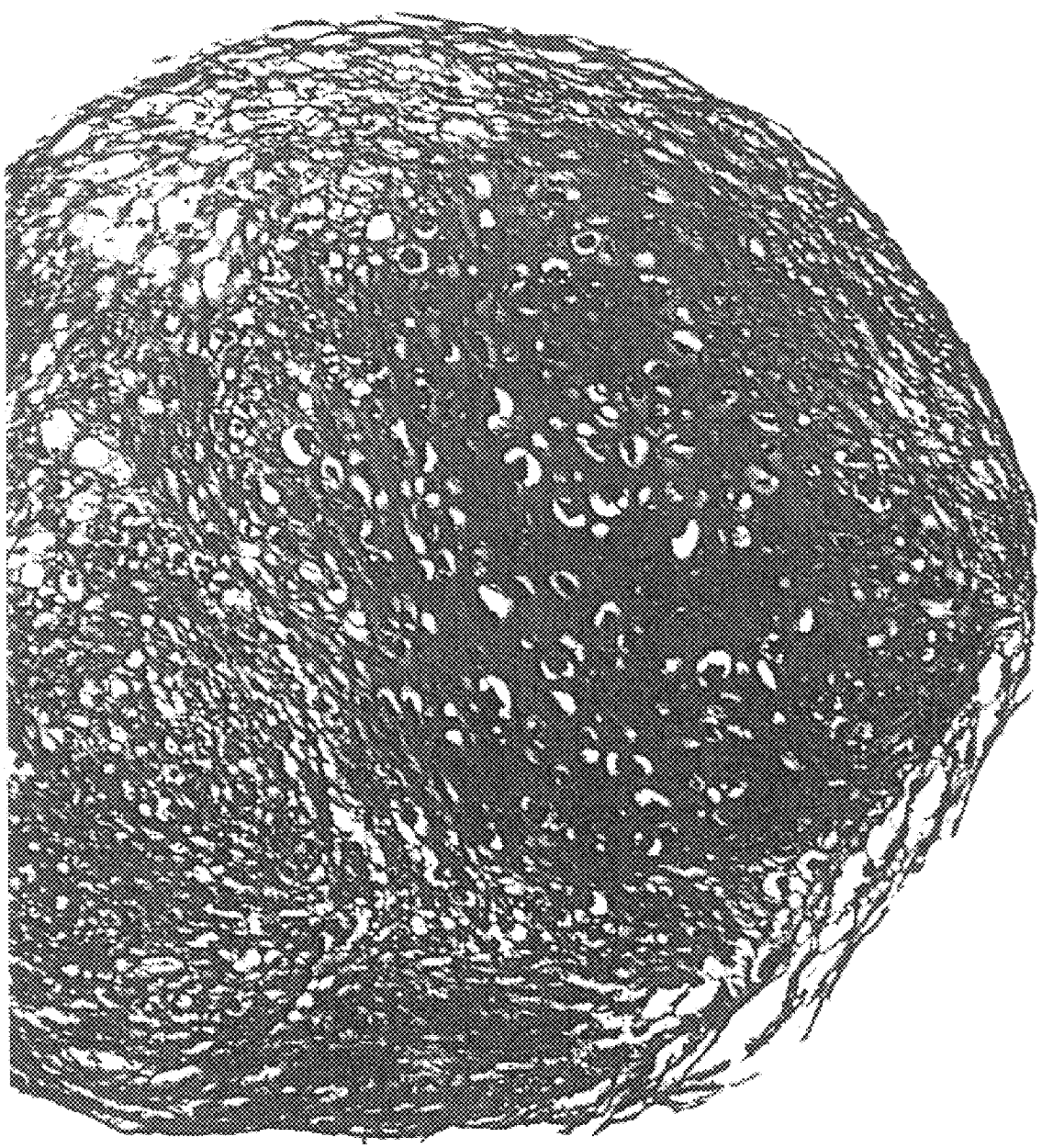
Figure 7C:
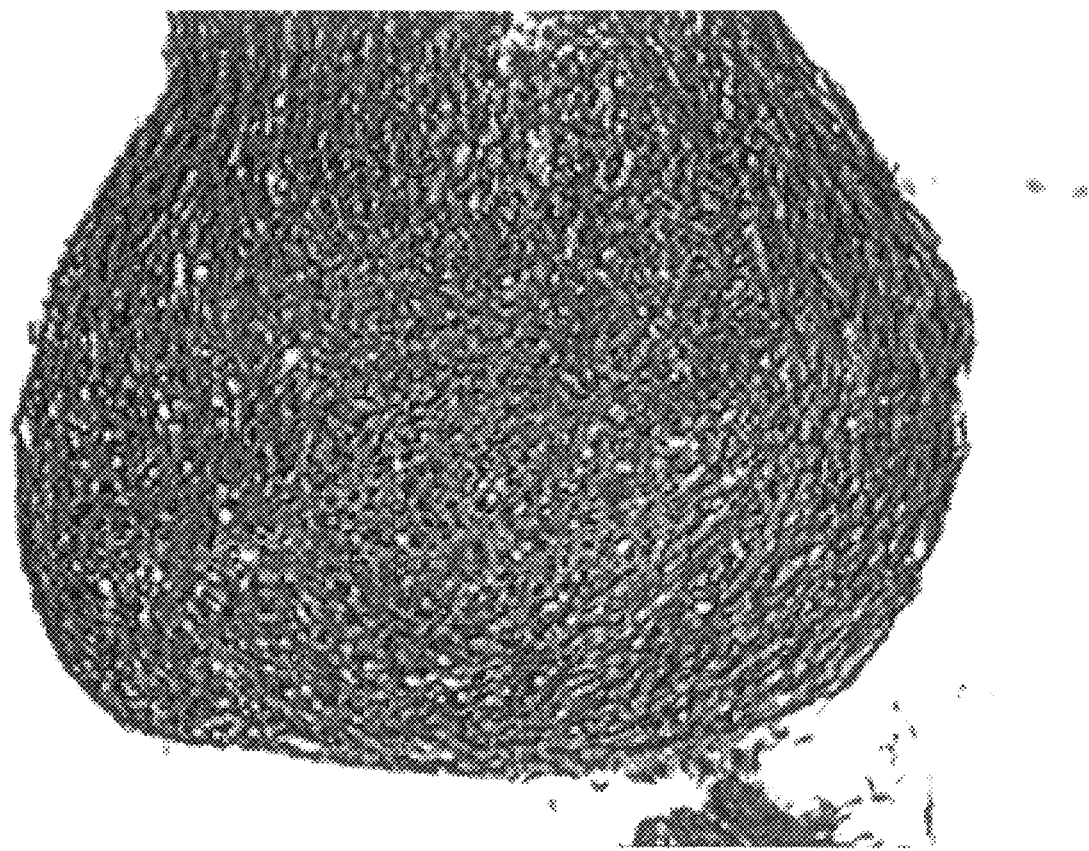
Figure 7D:
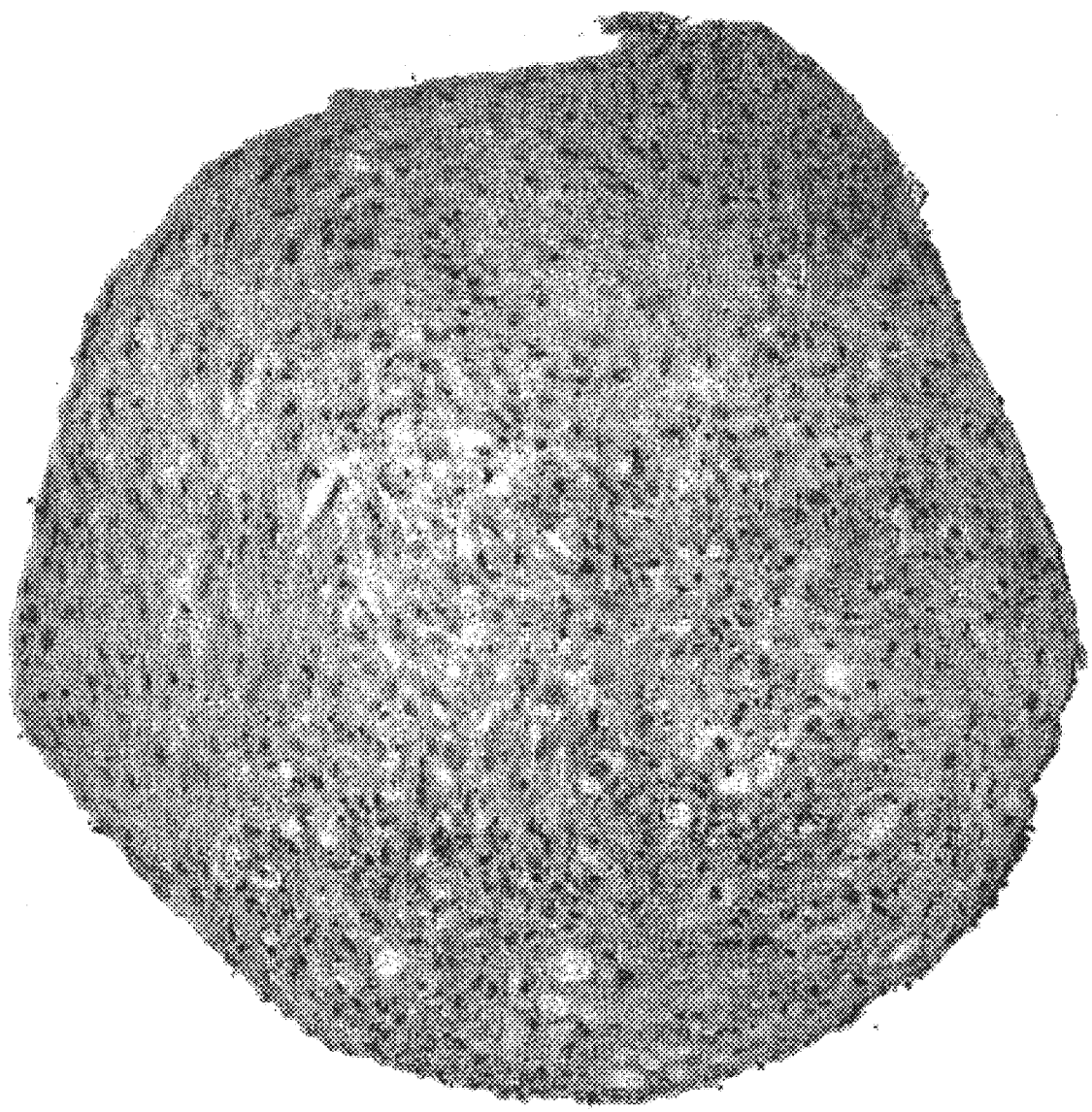
Figure 7E:
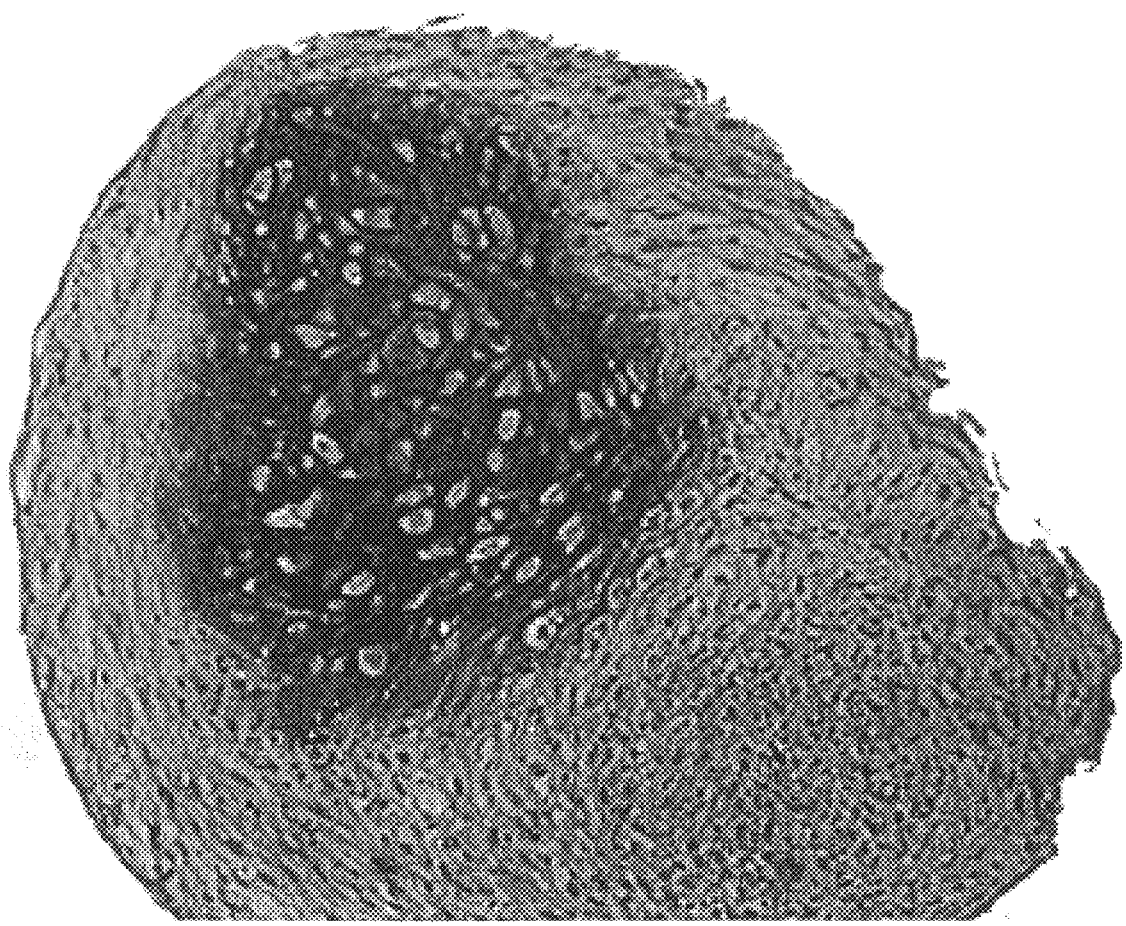
Figure 7F:
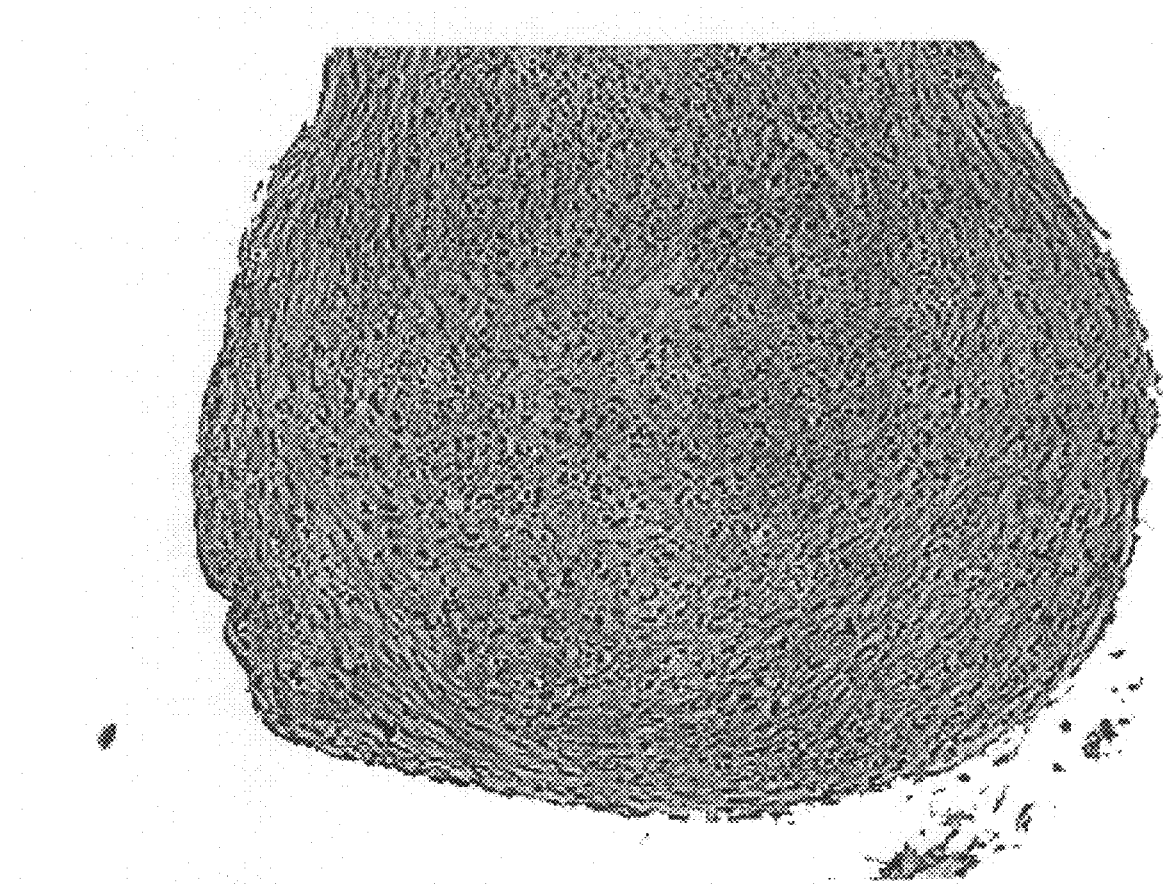

FIGS. 7D, 7E and 7F. MSCs were seeded onto ACP gel at concentrations of (FIG. 7D) 0.25, (FIG. 7E) 0.5 and (FIG. 7F) 1.0% and grown in culture for 11 days. Sections were tested for reactivity with a collagen II—specific antibody. FIG. 7D is shown above and FIGS. 7E and F on the following page.

Figure 8A:
Figure 8B:
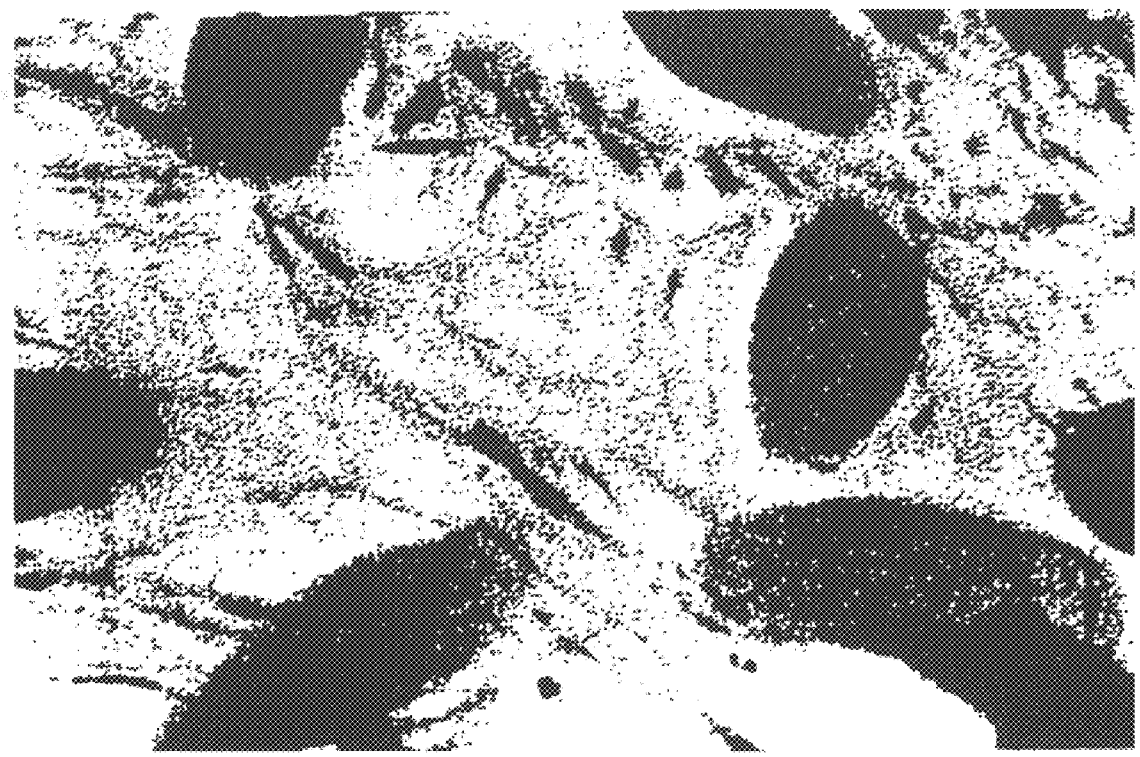

FIGS. 8A and 8B: Photomicrographs of representative histological sections of a hMSc loaded HYAFF 11 non-woven fabric cultured in osteogenic medium for 13 days (H&E stain), showing cell distribution.

Figure 9A:
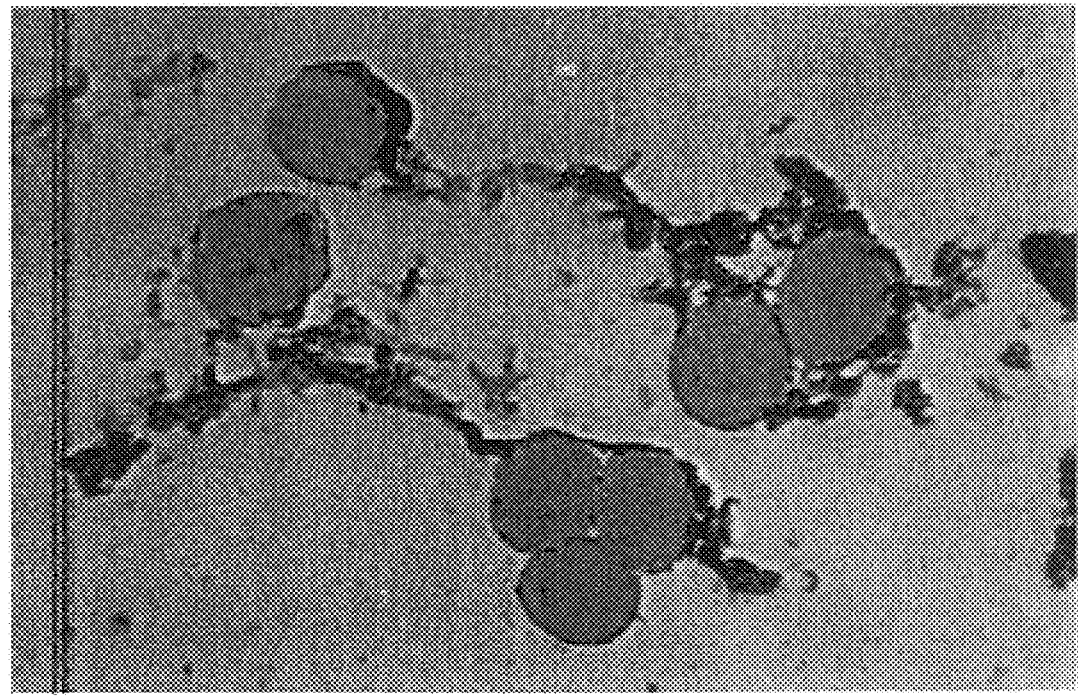
Figure 9B:
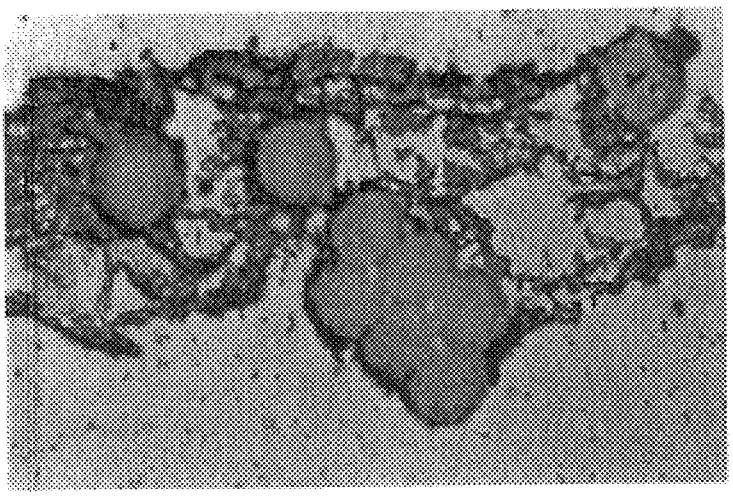

FIGS. 9A and 9B represent the immunohistochemical marking of Collagen I with monoclonal antibodies (avidin/biotin 200×) of (FIG. 9A) HYAFF 11 nonwoven fabric in which human fibroblasts from bone marrow mesenchyma have been seeded and compared with (FIG. 9B) HYAFF 11 non-woven fabric in which human fibroblasts of dermal origin have been seeded. In both cases (FIGS. 9A and 9B), after 2 week cultures the presence of type I collagen can be observed.

Figure 10A:
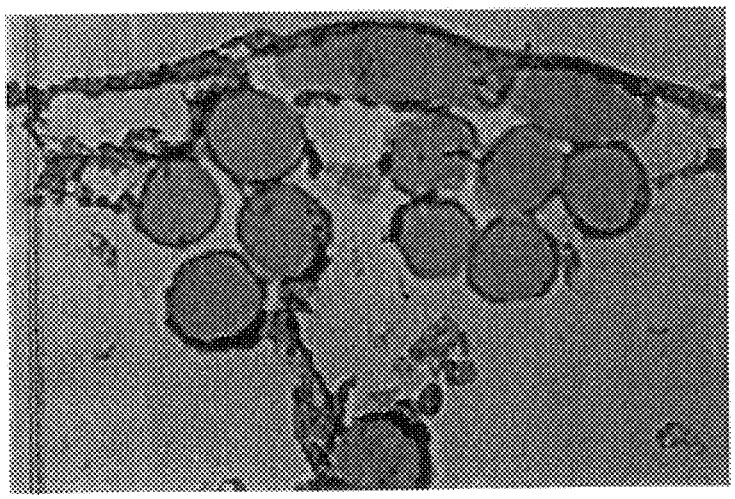
Figure 10B:
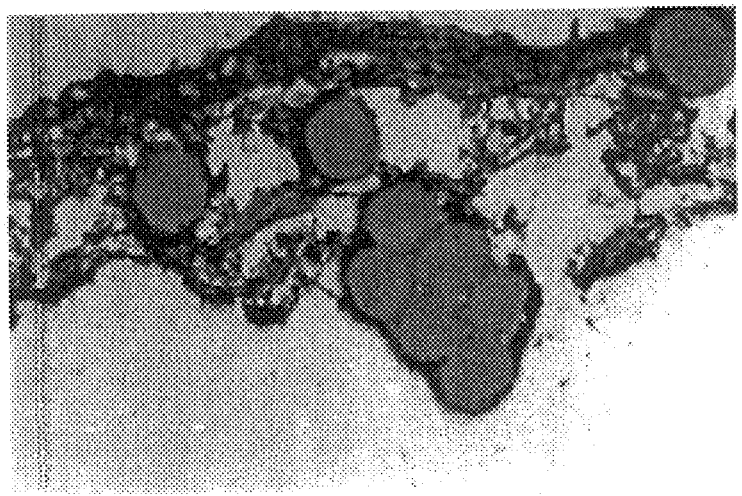

FIGS. 10A and 10B represent the immunohistochemical marking of collagen III with monoclonal antibodies (avidin/biotin 200×) of, respectively, (FIG. 10A) HYAFF 11 non-woven fabric with bone marrow mesenchyma fibroblasts 2 weeks after seeding, in comparison with (FIG. 10B) HYAFF 11 nonwoven fabric with fibroblasts of dermal origin 2 weeks after seeding. In both cases there is a marked positivity to the reaction.

Figure 11A:
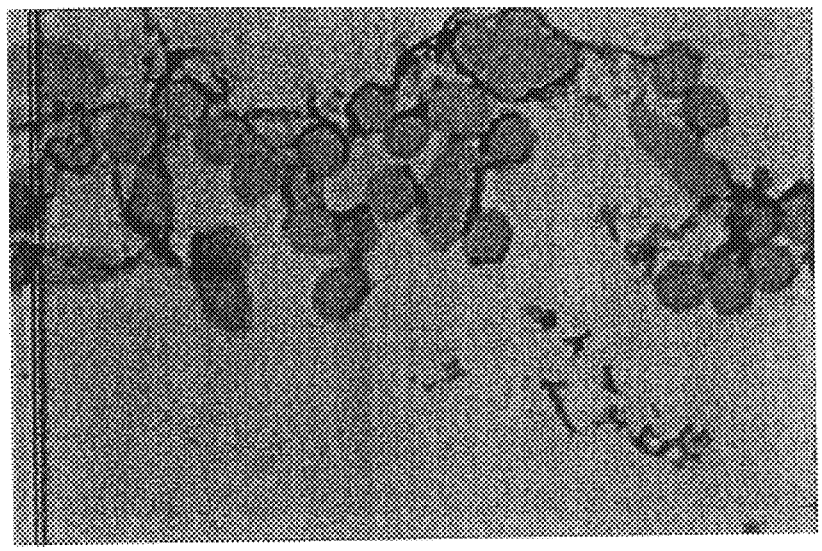
Figure 11B:
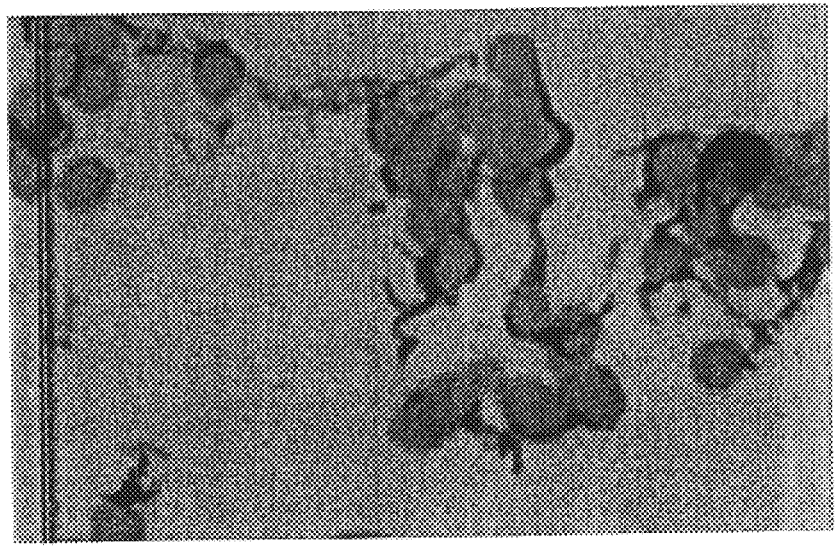

FIGS. 11A and 11B represent the immunoreaction with collagen IV with monoclonal antibodies (avidin/biotin 100×) of, respectively, (FIG. 11A) HYAFF 11 nonwoven fabric with bone marrow mesenchyma fibroblasts 2 weeks after seeding, in comparison with (FIG. 11B) HYAFF 11 nonwoven fabric with fibroblasts of dermal origin 2 weeks after seeding. The two different types of fibroblasts express collagen IV synthesis in the same manner.

Figure 12A:
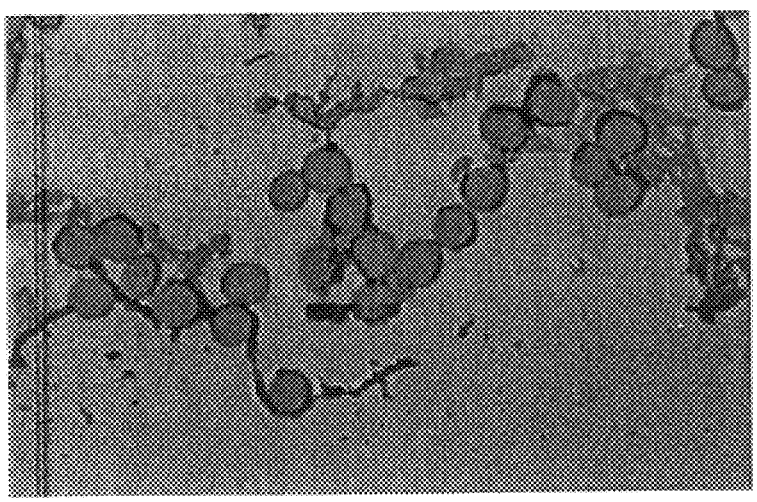
Figure 12B:
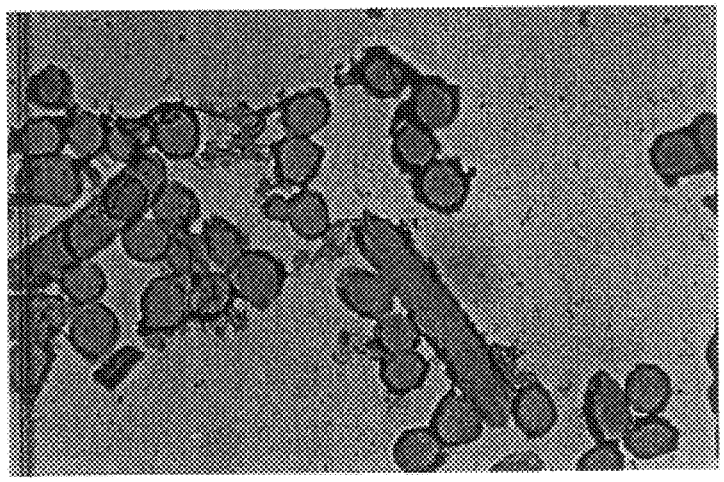

FIGS. 12A and 12B represent the immunohistochemical marking of fibronectin with monoclonal antibodies (avidin/biotin 100×) of, respectively, (FIG. 12A) HYAFF 11 non-woven fabric with bone marrow mesenchymal fibroblasts 2 weeks after seeding, in comparison with (FIG. 12B) HYAFF 11 nonwoven fabric with fibroblasts of dermal origin 2 weeks after seeding. Positivity to immunoreaction is marked in both types of fibroblasts.

Figure 13A:
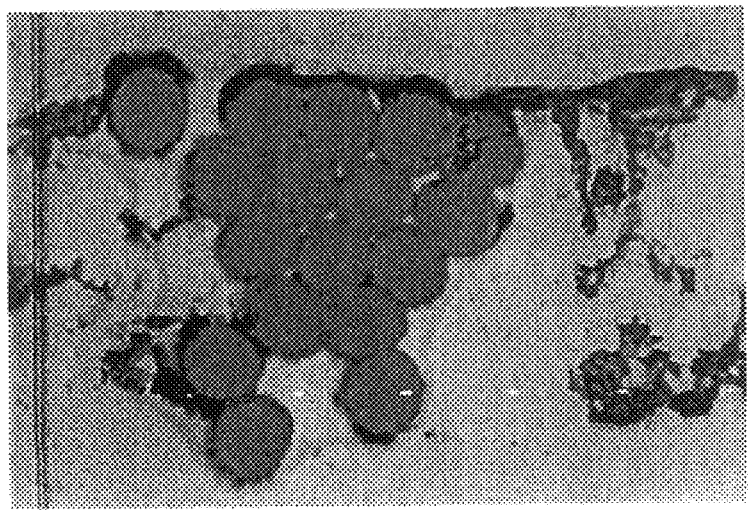
Figure 13B:
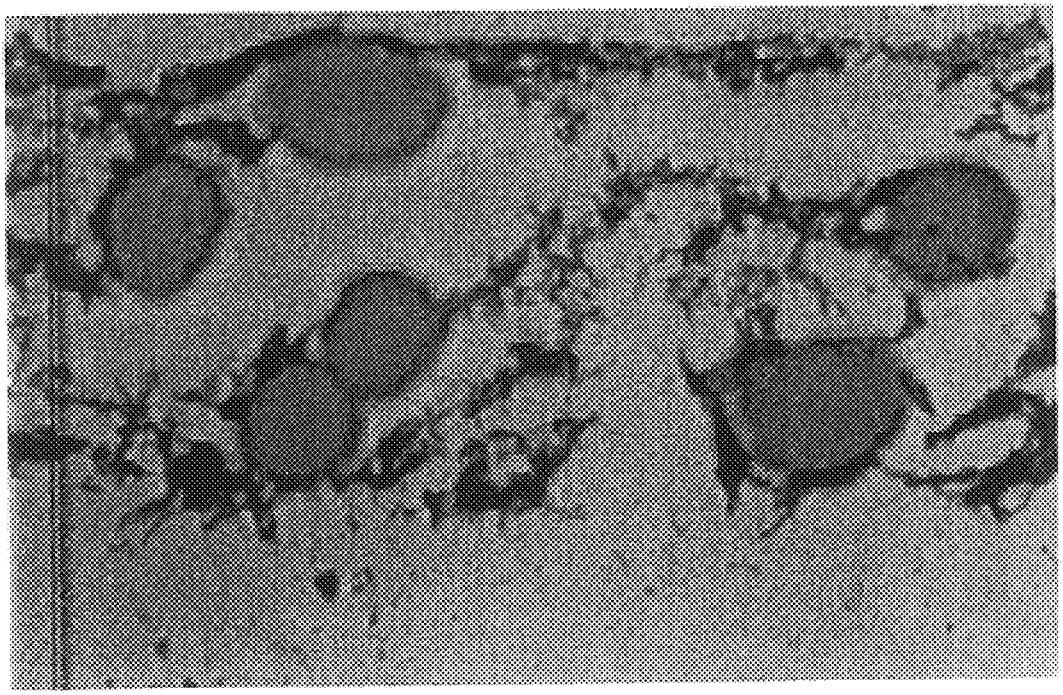

FIGS. 13A and 13B represent immunohistochemical marking of laminin with monoclonal antibodies (avidin/biotin: 200×) of, respectively, (FIG. 12A) HYAFF 11 non-woven fabric with bone marrow mesenchymal fibroblasts 2 weeks after seeding, in comparison with (FIG. 12B) HYAFF 11 nonwoven fabric with fibroblasts of dermal origin 2 weeks after seeding. The presence of laminin is very clear in both types of cultures.

DETAILED DESCRIPTION OF THE INVENTION

The cell preparation a) of the biological material according to the present invention, can be, for example, a human bone marrow peripheral blood or cord blood isolate or more generally a mesenchymal tissue extract enriched as to the proportion of mesenchymal stem cells therein. In a preferred embodiment, the cell preparation is an isolated, homogeneous population of mesenchymal stem cells. The isolated mesenchymal stem cells of human or other animal origin and from marrow or other sites of mesenchymal origin can be autologous, allogeneic, or from xenogeneic sources and can be embryonic or from post-natal sources. Bone marrow cells may be obtained from iliac crest, femora, tibiae, spine, rib or other medullar spaces. Other sources of human mesenchymal stem cells include embryonic yolk sac, placenta, umbilical cord, periosteum, fetal and adolescent skin, muscle and blood. In order to obtain mesenchymal stem cells, it is necessary to isolate rare pluripotent mesenchimal stem cells from other cells in bone marrow or other mesenchymal stem cell sources.

The term "isolated" means altered "by the hand of man" from the natural state; i.e. anything that occurs in nature is defined as isolated when it has been changed or removed from its original environment, or both. With respect to a human mesenchymal stem cell (hMSCs), it is isolated when it has been removed from a donor's body. In one contemplated sense, this is true even when the hMSC is still in a mixed cell population. In another contemplated sense, the hMSC is treated to separate it from other types of cells, such as differentiated mesenchymal cells or hematopoietic cells such as are found, for example, in bone marrow. Such a procedure is fully disclosed in U.S. Pat. No. 5,486,359, which we incorporate herewith by reference.

As the term is employed herein, for example a naturally occurring polypeptide naturally present in a living animal in its natural state is not "isolated", but the same polypeptide separated from the coexisting materials of its natural state is "isolated".

The three-dimensional matrix (b) in the biological material of the present invention is preferably in the form of gel, woven or non-woven tissue or fabric, sponges, guide channels, gauzes.

More preferably it is in the form of a nonwoven tissue, sponges, gel, microspheres, granules.

The three-dimensional matrix of the biological material according to the present invention can contain the hyaluronic acid derivative in combination with hyaluronic acid as such and/or another biocompatible material, or alternatively it can be formed solely by at least one of said hyaluronic acid derivatives.

A biocompatible material different from hyaluronic acid and its derivatives, optionally contained in the three-dimensional matrix is preferably resorbable gelatin, cellulose and/or collagen based matrices, and/or synthetic polymers such as polylactic or polyglycolic acid in turn in combination with bone marrow and/or isolated mesenchymal stem cells.

According to a preferred embodiment, the three-dimensional matrix is formed by fibrous webs of a hyaluronic acid derivative interwoven with fibrous webs of a bioresorbable material other than a hyaluronic acid derivative.

Preferably the hyaluronic acid derivative contained in the three-dimensional matrix of the biological material of the present invention is a partial or complete ester of hyaluronic acid with an aliphatic, aromatic or araliphatic alcohol (HYAFF) like those disclosed in U.S. Pat. No. 4,851,521 we incorporate herewith by reference, or a crosslinked hyaluronic acid derivatives (ACP) like those disclosed in U.S. Pat. No. 5,676,964, we incorporate herewith by reference.

The hyaluronic acid esters used for preparing the three-dimensional matrix according to the present invention have preferably a degree of esterification comprised between 25 and 100%. More preferably, the hyaluronic acid esters used are the partial or complete benzyl esters. According to a particularly preferred embodiment, hyaluronic acid benzyl esters are used having a degree of esterification respectively of 75% (HYAFF-11-p75) and 100% (HYAFF 11).

The nonwoven tissue of hyaluronic acid esters and ACP is preferably prepared by the process disclosed in U.S. Pat. No. 5,520,916 we incorporate herewith by reference.

The hyaluronic acid eater sponges are preferably prepared by the process disclosed in U.S. Pat. No. 5,503,848, we incorporate herewith by reference.

The nonwoven tissue of ACP may be prepared by the same process disclosed in the above mentioned U.S. Pat. No. 5,520,916.

The biological material according to the present invention may therefore assume the form of the specific three-dimensional matrix by which it is composed.

The biological material according to the present invention can also contain additional components, such as differentiation inductive agents, which are able therefore to direct and enhance the differentiation of the mesenchymal stem cells therein into a desired mesenchymal lineage. Such bioactive factors or combinations of factors are effective to induce differentiation of MSCs in the biological material according to the present invention into a mesenchymal lineage selected from the group consisting of osteogenic, chondrogenic, tendonogenic, ligamentogenic, myogenic, marrow stromagenic, adipogenic, dermagenic. Preferably, the cells are contacted ex vivo, with one or more bioactive factors in this aspect, thereby providing a method free of any part risk, said method being optionally associated with in vivo administration of any bioactive factors.

In specific examples, the bioactive factor is a member of the transforming growth factor-b family (TGF-b), such as $TGF-b_1$ or $TGFb_3$ and the human MSCs are directed into the chondrogenic lineage; the bioactive factor is interleukin 1 and the human MSCs are directed into the stromal cell lineage (preferably the interleukin 1 is interleukin 1a); the bioactive factors are dexamethasone, ascorbic acid-2-phosphate and b-glycerophosphate and TGF superfamily proteins such as the morphogenic proteins (BMPs) and the human MSCs are directed into the osteogenic lineage; or the bioactive factor is selected from the group consisting of 5-azacytidine, 5-azadeoxycytidine and analogs of either of them and the human MSCs are directed into the myogenic lineage, the bioactive factor is a fibroblast growth factor, such as basic Fibroblast Growth Factor, and the cells are directed to the dermagenic lineage.

The above mentioned composition containing the biological material according to the present invention can contain pharmaceutically acceptable ingredients such as antibiotic, antimycotic, antiinflammatory, immunosuppressive, and/or other types of therapeutic, preservative and excipient agents or diluents well known to those skilled in the art.

The therapeutic and surgical methods according to the present invention, for treating a mesenchymal tissue defect in an animal, particularly a mammal, and more particularly a human in need thereof according to the present invention comprise respectively the administration of the above mentioned composition and implant. Custom cell-matrix implants containing autologous, allogeneic, xenogeneic bone marrow and/or MSCs can be administered by using open surgical techniques, arthroscopic techniques or percutaneous injection.

The key to effective clinical outcomes using MSC therapy, is to provide that number of enriched or culture-expanded mesenchymal stem cells to the patient, or such suitable numbers in the optimised matrix, which repairs or replaces the bone or other tissue defect beyond that in a volume of whole marrow equivalent to that of the defect. This is referred to as the "Regenerative MSC Threshold", or that concentration of MSCs necessary to achieve direct repair of the tissue defect. The Regenerative MSC Threshold will vary by 1) type of tissue (i.e., bone cartilage, ligament, tendon, muscle, marrow stroma, dermis and other connective tissue); 2) size or extent of tissue defect; 3) formulation with pharmaceutical carrier; and 4) age of the patient.

The actual amount and formulation of the biological material or the composition thereof to be administered will depend on various factors such as the severity of the wound, the condition of the patient, the age of the patient and any collateral injuries or medical ailments possessed by the patient.

The biological material according to the present invention, the composition and implant thereof may be prepared by soaking the three-dimensional matrix in a cell suspension of MSCs, mixed cell population containing MSCs, MSC-enriched mesenchymal stem cells suspensions or modified fractions of whole marrow, where the suspension liquid can have other active ingredients dissolved therein.

Alternatively, in particular when the three-dimensional matrix is a sponge, a predetermined amount of a cell suspension can be transferred on top of a sponge matrix, and the cell suspension can be absorbed. In addition, by varying the ratio of the components in said biodegradable matrices, the surgical handling properties of the cell biomatrix can be adjusted in a range from a dimensionally stable matrix, to a moldable putty-like consistency to a pliable gel or slurry, to a powder or to an injectable fluid.

It is contemplated that from about 50,000 to about $20 \times 10^6$ MSCs in or with each ml (liquid) or cc (solid) of matrix would be used. Preferably the number of MSCs is in the range of about $15-20 \times 10^6$ MSCs per ml or cc. The three dimensional matrix can be from about 0.01% to about 10% hyaluronic acid ester, preferably from about 2% to about 6%. It is contemplated that each ml or cc matrix will include from about 20 to about 200 mg of hyaluronic acid ester.

EXAMPLE 1

Support of In vitro Chondrogenesis of Human Bone Marrow-derived MSCs

Methods

MSCs were prepared from bone marrow taken from a normal human donor using standard techniques (Hainesworth, S. E. Baber, M. A., Caplan, A. I. (1992) Bone, 13:69–80),(Jaiswal, N., Haynesworth S. E. Caplan, A. I. and Bruder, S. P. (1997)J.Cell.Biochem. 64, 295–312). After growth in primary culture for a period of 14 days the cells were treated with trypsin and prepared as a suspension of $2 \times 10^7$ cells/ml of medium (10% fetal bovine serum in DMEM-LG). This corresponds to 200,000 cells/10 $\mu l$.

HYAFF 11 Sponge. HYAFF 11 sponge disk (2 mm high×1.5 cm diameter) was removed from its packing under sterile conditions and was cut with a scalpel into pieces approximately 2 mm×2 mm×3 mm (=12 $\mu l$). The cells were washed in chondrogenic medium (CM) (particularly, CMEM with ITS, ascorbate-2-phosphate, dexamethasone and TGF b3) (Johnstone, B., Yoo, J. U. and Barry F. P. (1996) Trans. Orthop. Res. Soc. 21, 65), (Barry F. P., Johnstone, B., Pittenger, M. F., MacKay A. M., and Murphy J. M. (1997) Trans. Orthop. Res. Soc 22,228), resuspended in the same medium and then added to the piece of HYAFF 11. 10 $\mu l$ of suspension, containing 200,000 cells, was added to each sponge piece. The droplet did not immediately absorb on the HYAFF but remained on the surface for a short time. After 1 hour the cell-loaded pieces of HYAFF 11 were placed in a 6 well plate (2 per well) and covered with 1 ml CM.

HYAFF 11 FABRIC: Non-woven HYAFF 11 fabric (10 cm×10 cm) was also used. This was cut into pieces of 5 mm×5 mm and was used in the same way as the sponge. 10 µl of cell suspension containing 200,000 cells were added to each piece of cut fabric. After 1 hour the pieces ware placed in 6 well plates and covered with 1 ml medium.

ACP Gel:200,000 cells in 10 µl CM were placed at the bottom of a 15 ml sterile tube. 200 µl of ACP gel was loaded into a sterile 1 ml syringe. Approximately 25 µl of the gel was extruded from the tip of a 16 gauge needle and placed on top of the cell suspension. Cells and gel were mixed with the needle and then centrifuged briefly at low speed. The cell-ACP suspension was overlaid gently with a ml CM. Cell-ACP suspensions were prepared using both 3% and 6% ACP gels. In all case cultures were established using 200, 000 cells. Control cultures consisted of cells grown in standard chondrogenic pellet format. The cells were set up as shown in Table 1.

TABLE I

|   | Material | n. | time (days) |
|---|----------|----|-------------|
| 1 | HYAFF 11 sponge | 2 | 7 |
| 2 | HYAFF 11 sponge | 2 | 14 |
| 3 | HYAFF 11 sponge | 2 | 21 |
| 4 | HYAFF 11 non-woven | 2 | 7 |
| 5 | HYAFF 11 non-woven | 2 | 14 |
| 6 | HYAFF 11 non-woven | 2 | 21 |
| 7 | 3% ACP | 2 | 7 |
| 8 | 3% ACP | 2 | 14 |
| 9 | 3% ACP | 2 | 21 |
| 10 | 6% ACP | 2 | 7 |
| 11 | 6% ACP | 2 | 14 |
| 12 | 6% ACP | 2 | 21 |
| 13 | Control | 1 | 7 |
| 14 | Control | 1 | 14 |
| 15 | Control | 1 | 21 |

At the end of culture the materials were washed with 4 ml phosphate-buffered saline on ice for 30 min prior to fixation with formalin. They were embedded in paraffin, cut into 5 µm sections and stained with Toluidine blue. Additional sections were stained for collagen type II with monoclonal antibody C4F6 using standard immunocytochemical techniques (Srinvias, G. R., Barrach, H. J. and Chichester, C. O. (1993) J. Immunol. Meth. 159, 53–62)

Results

Handling properties: Both the sponge and fabric had excellent handling properties and were easily cut into pieces of the required length and shape. The sponge showed a poor ability to absorb the cell suspension. The fabric absorbed the cell suspension more rapidly than medium alone.

Figure 1A:
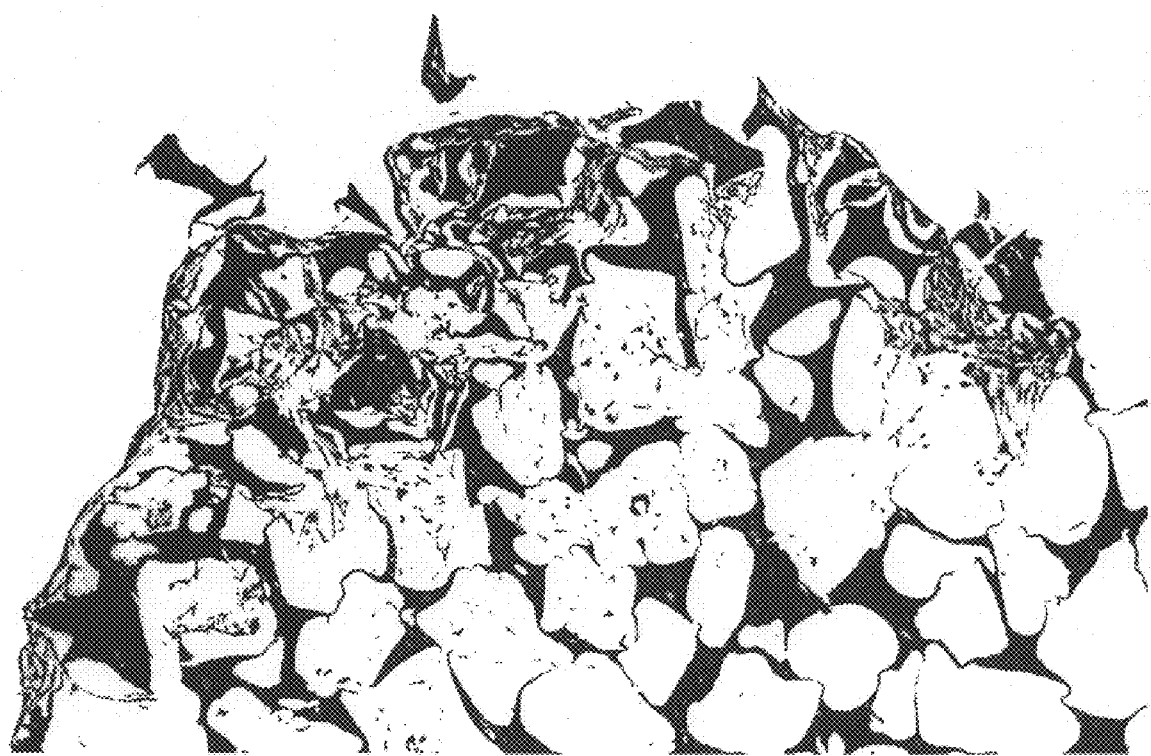
FIGS. 1A and 1B HYAFF 11 sponge (2 mm×2 mm 3 mm) was seeded with 200,000 mesenchymal stem cells and cultured in Chondrogenic Medium (CM) for 7 days. Sections were stained with Toluidine blue. Original magnification 4× (FIG. 1A) or 10× (FIG. 1B).
Figure 1B:
Figure 1C:
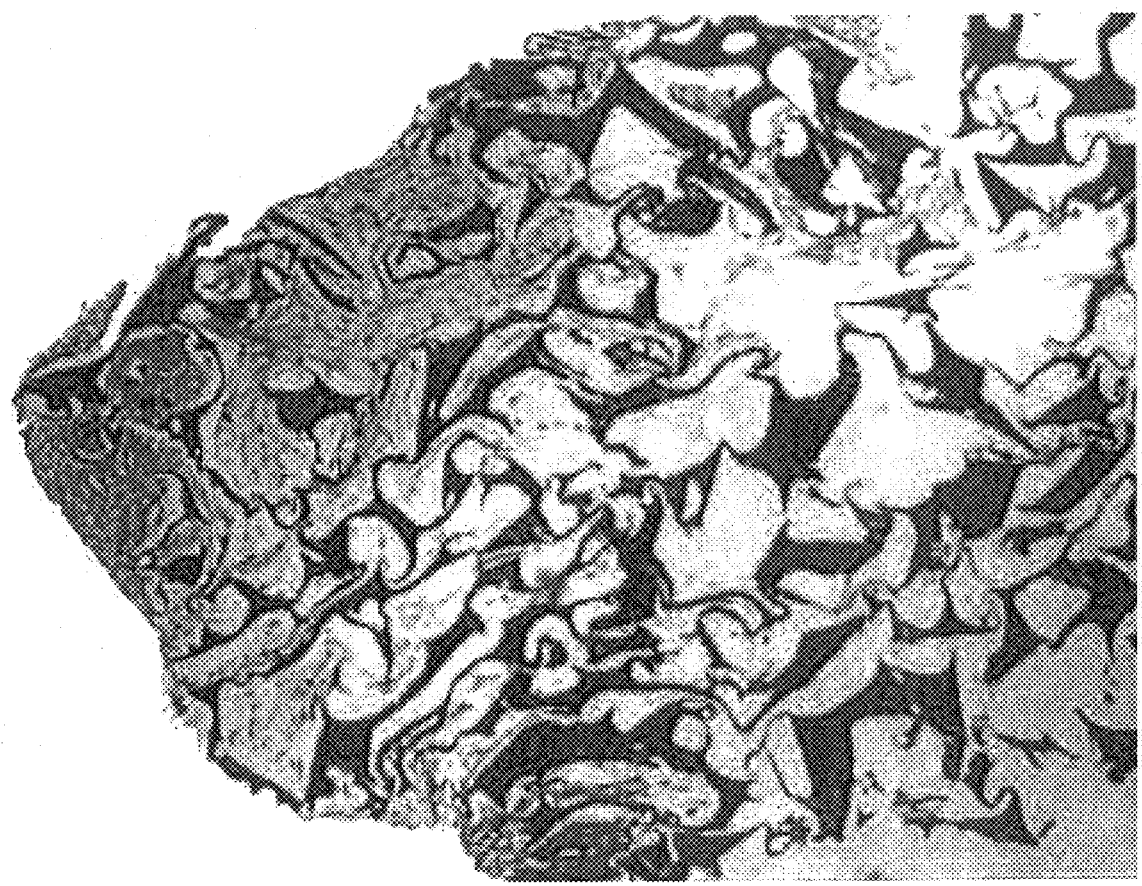
FIG. 1C HYAFF 11 sponge (2 mm×2 mm×3 mm) was seeded with 200,000 mesenchymal stem cells and cultured in CM for 15 days. Sections stained with Toluidine blue at original magnification 4×.

HYAFF 11 Sponge: The histological sections showed that the sponge material did not become fully seeded with cells (FIGS. 1A–1C). It may be possible to improve this if a vacuum is applied to remove air trapped in the pores therefore allowing for more efficient penetration of cells.

Figure 2A:
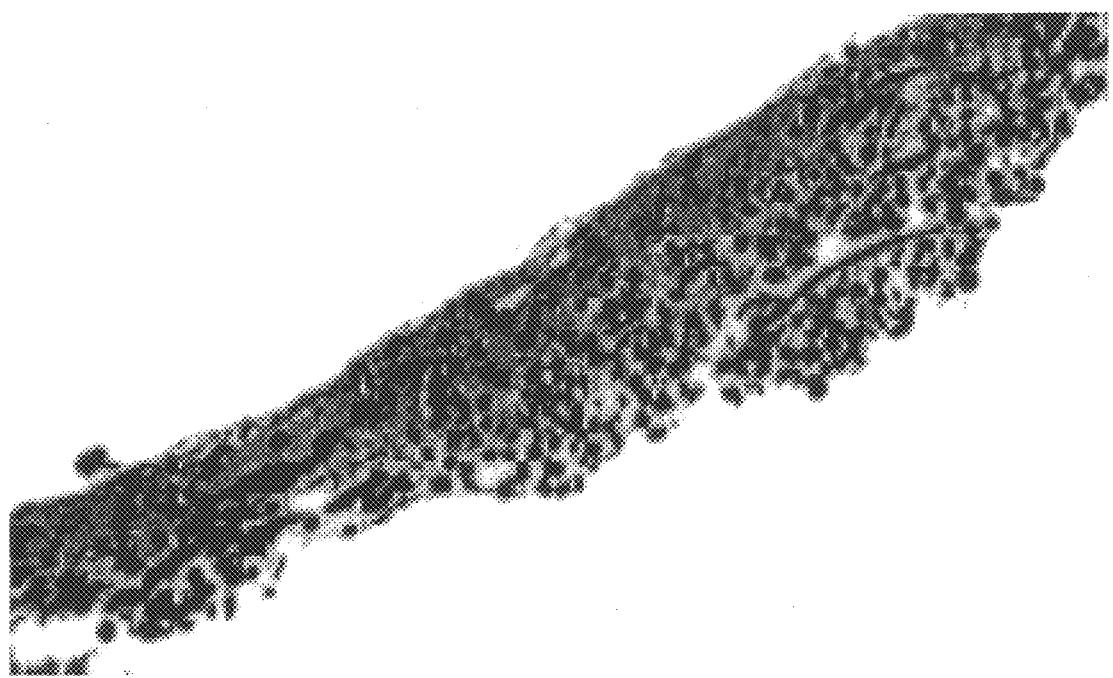
FIGS. 2A and 2B HYAFF 11 non-woven fabric(0,5 cm×0,5 cm)seeded with 200,000 mesenchymal stem cells and cultured for 21 days with Toluidine blue at 4× (FIG. 2A) or 10× (FIG. 2B) original magnification.
Figure 2B:
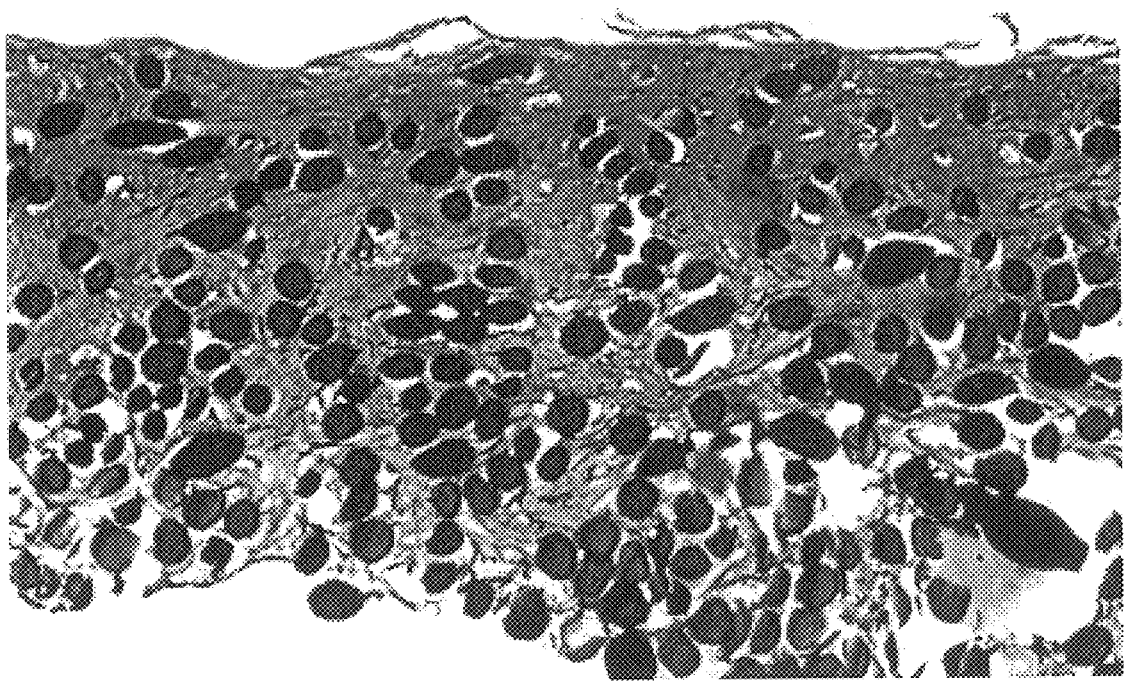
Figure 2C:
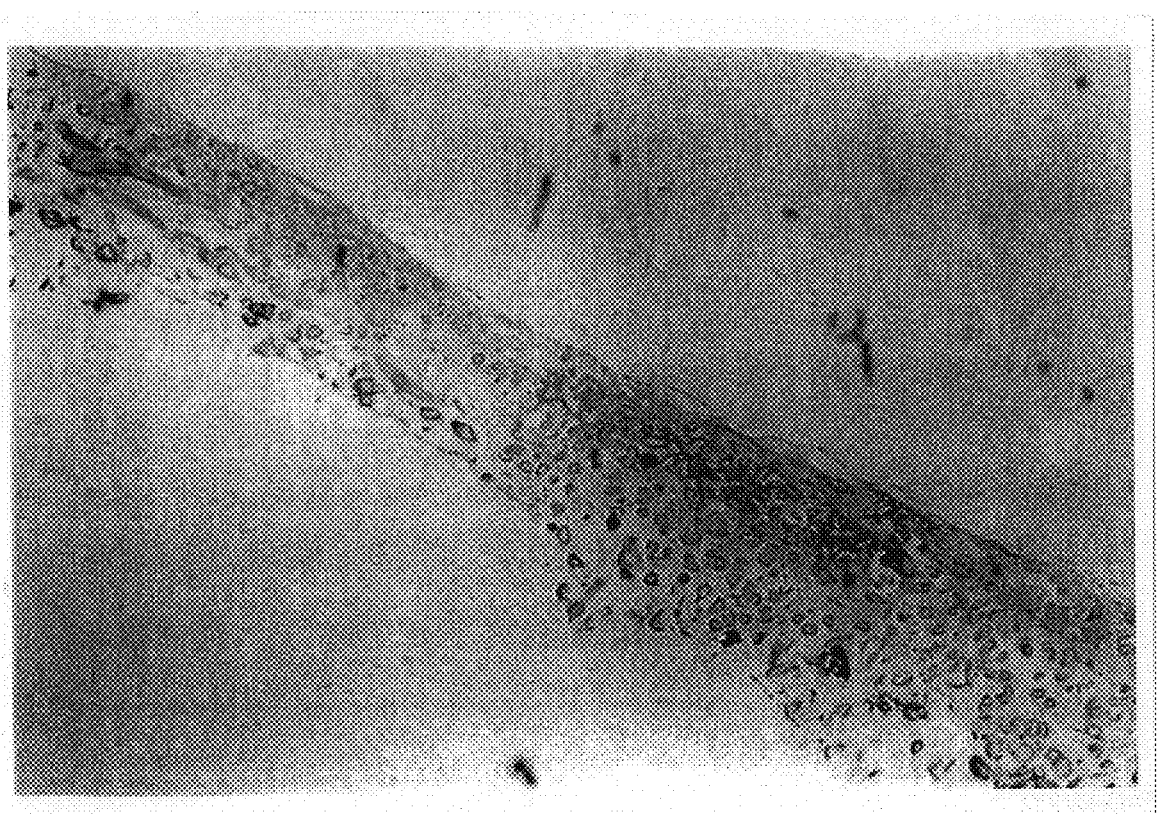
FIG. 2C HYAFF 11 non-woven fabric (0,5 cm×0,5 cm) seeded with 200,000 mesenchymal stem cells and cultured for 21 days with a type II collagen-specific antibody, 4× original magnification.

HYAFF 11 Fabric: This became seeded with a layer of cells which became confluent and which were Toluidine blue positive (FIGS. 2A–2B). They also expressed type II collagen after 7 days in culture.

Figure 3A:
FIGS. 3A and 3B Mesenchymal stem cells grown in the presence of ACP gel 3% for 7 days (FIG. 3A). and 21 days (FIG. 3B) stained with Toluidine blue. These cultures stained strongly for type II collagen-specific antibody, (over top) and to showed more uniform and better morphology than control pellets.
Figure 3B:
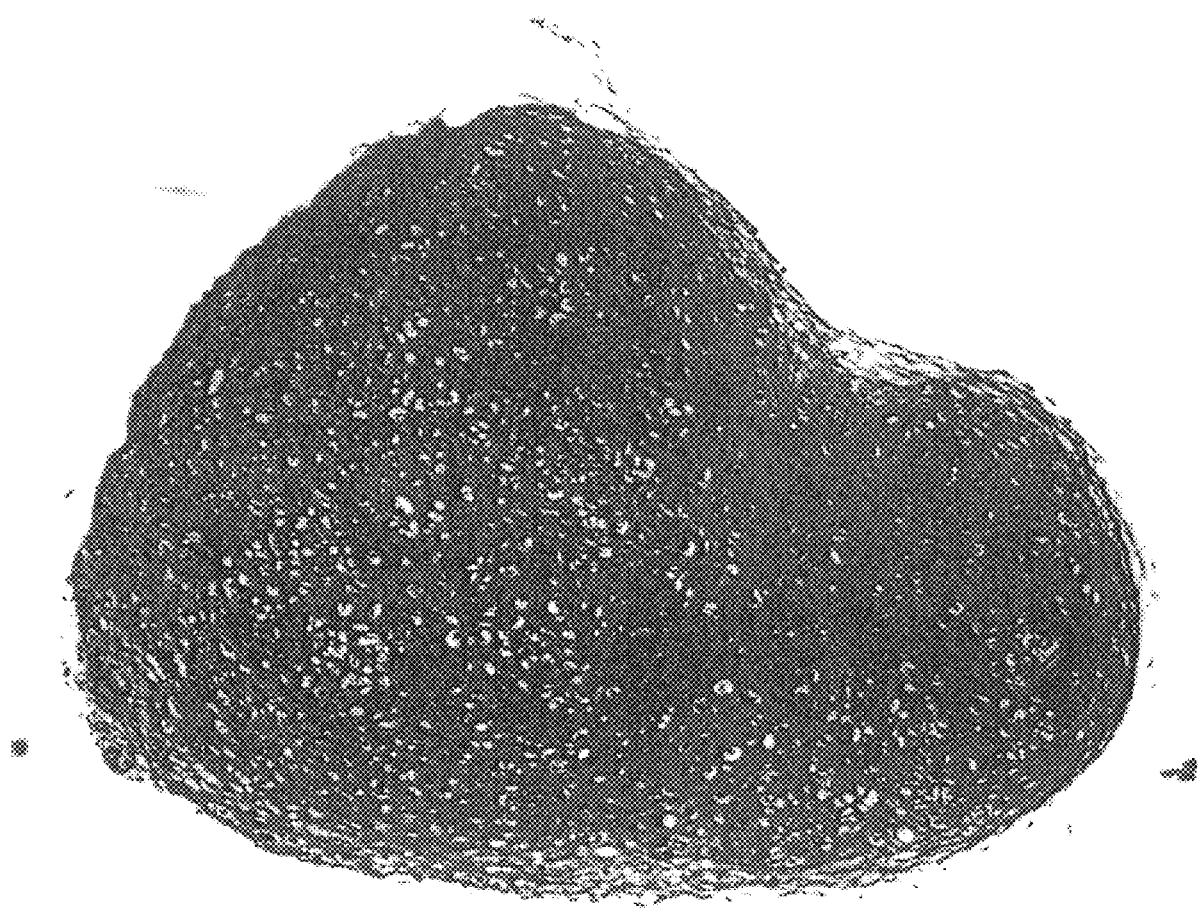
Figure 3C:
FIGS. 3C and 3D. Cells grown in the presence of ACP 3% gel for 21 days (top) immunostained for type II collagen. These cultures showed more uniform staining and better morphology than control pellets (FIG. 3D bottom) cultured for the same time.
Figure 3D:
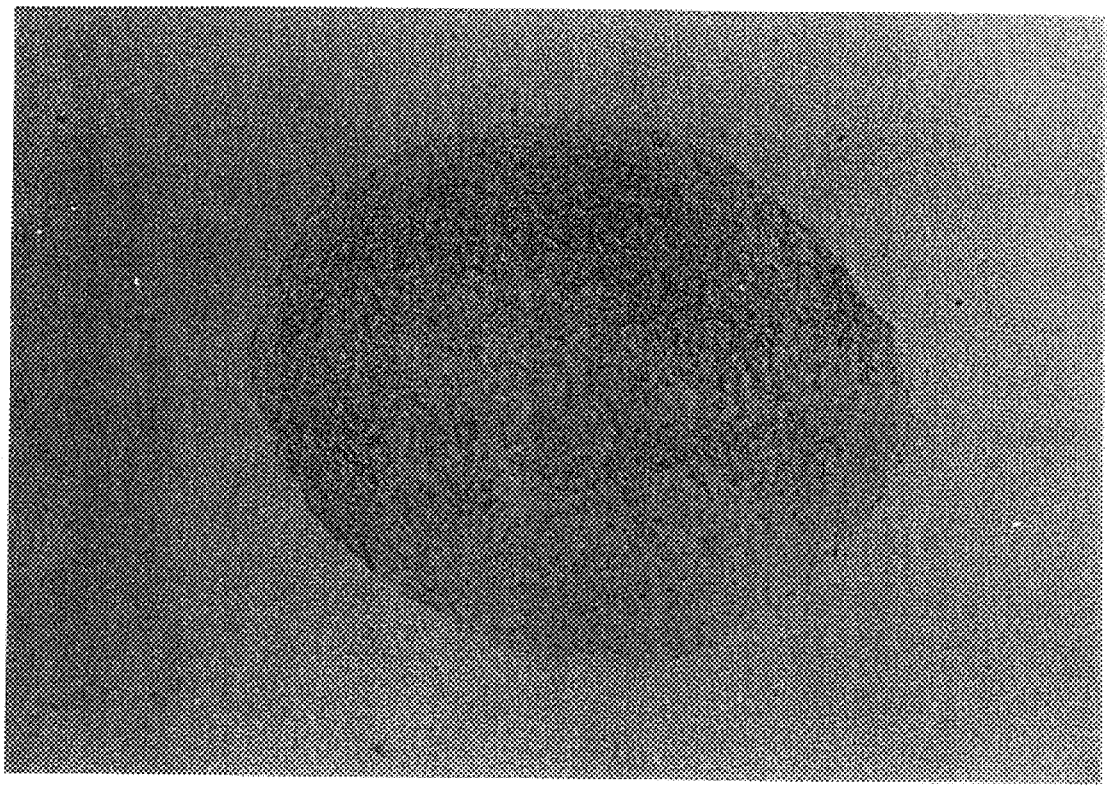

ACP Gel; During the first day in culture the gel layer showed yellow coloration, as if the ACP gel was inhibiting flow of nutrients to the cells. A clear interface was visible between cells and medium. In the case of both the 3 and 6% gels, the cells showed a high degree of matrix organisation after 7 days in culture and also showed intense metachromatic staining with Toluidine blue (FIGS. 3A–3D). These cells were also strongly positive for type II collagen. In the presence of 3% gel the cultures showed an unusual modular morphology (FIG. 3A) which was still evident at 21 days (FIG. 3B). All cultures grown in the presence of ACP gel expressed abundant type II collagen (FIG. 3C) at 21 days. The morphology of these pellets was similar to or better than control pellets (FIG. 3D).

Conclusions

These experiments show that these materials are compatible with growth and chondrogenic differentiation of human MSCs. In general terms their handling properties are good and the handling characteristics of the ACP gel are improved by the use of a suitable device. These results demonstrate that these materials have utility as delivery biomatrices in vivo, especially in the area of cartilage repair.

EXAMPLE 2

Support of In vitro Chondrogenesis of Human Bone Marrow-derived MSCs

In a second series of experiments the ability of these materials to support MSC chondrogenesis in vitro was further explored.

Methods

HYAFF 11 Sponge. HYAFF 11 sponge material was cut into pieces 2×2×3 mm, placed in 2 ml sterile water in 11×75 mm polypropylene culture tube and sonicated for 30 seconds. The water was replaced with 2 ml CM: (DMEM Gibco BRL) supplemented with 1 mM sodium pyruvate (Sigma) 0.1 mM ascorbate-2-phosphate (Wako). $1 \times 10^7$ M dexamethasone (Sigma), 1% ITS+ (Collaborative Biomedical Products) and 10 ng/ml recombinant human TFG-b3 (R+D Systems)).

The sponge pieces were degassed by inserting a 2 ml syringe and drawing back the plunger. The tube was tapped gently to free from the surface. The sponge remained in CM until it was used further.

MSCs were prepared from bone marrow from a normal human donor (Hainesworth, S. E. Baber, M. A., Caplan, A. I. (1992) Bone, 13:69–80),(Jaiswal, N., Haynesworth S. E. Caplan, A. I. and Bruder, S P. (1997)J.Cell.Biochem. 64, 295–312). The cells were suspended at a density of $1.8 \times 10^6$ cells/ml in CM. Suspension (250 µl) was loaded onto the sponge, which was then evacuated as described above to allow the cells to penetrate the material. This procedure was carried out on 9 pieces of sponge. The sponge pieces were placed in 9 individual polypropylene tubes and covered with 0.5 ml CM. They were incubated at 37° C. in a 5% $CO_2$ atmosphere. Medium was changed every 3 days. Samples was harvested at 3, 11, 15 and 21 days.

HYAFF 11 Fabric. The fabric was wetted with sterile water and cut into 1.5×2 mm pieces. Each piece was placed in a 15 ml polypropylene tube and 20 µl cell suspension (containing 200,000 cells) was pipetted directly on to the fabric. The cells were allowed to sit for 1 hour at 37° C. before the addition of 1 ml of CM. Samples were harvested at 3, 15 and 21 days.

ACP Gel: The stock solution of hyaluronan gel (6% w/v, lot No. 108-95) was diluted with CM to give 1, 0.5 and 0.25% (w/v) gels. Cells ($3 \times 10^5$) were pelleted in a 15 ml tube by spinning at 500×g and 25 µl hyaluronan gel was added to each. 0.5 ml CM was added to each and the medium was changed every 3 days. Samples were harvested at 3, 11, 15 and 21 days.

Controls: MSCs from the same donor were cultured under standard chondrogenic conditions without added material. These cells (200,000/pellet) were maintained in CM (0.5 ml) and this was changed every 3 days.

Samples were narvested according to the schedule shown in Table II and were processed for histological analysis. Samples were washed with 4 ml cold PBS for 30 minutes and then placed in 1 ml of 10% neutral buffered formalin for 2 hours at room temperature. Pellets were washed twice with 4 ml PBS at room temperature, then placed in 70% ethanol for histological Processing. Sections of 5 µm were cut, stained with Toluidine blue, in some cases sections were immunostained for reactivity with an antibody specific for collagen type II

TABLE II

| Material | time (days) |
| --- | --- |
| HYAFF 11 sponge | 7, 11, 15, 21 (n = 3) |
| HYAFF 11 non-woven | 7, 11, 15, 21 (n = 3) |
| 0.25% ACP | 7, 11, 15, 21 (n = 2) |
| 0.5% ACP | 7, 11, 15, 21 (n = 2) |
| 1% ACP | 7, 11, 15, 21 (n = 2) |
| Control | 7, 11, 15, 21 (n = 3) |

Results

Figure 4A:
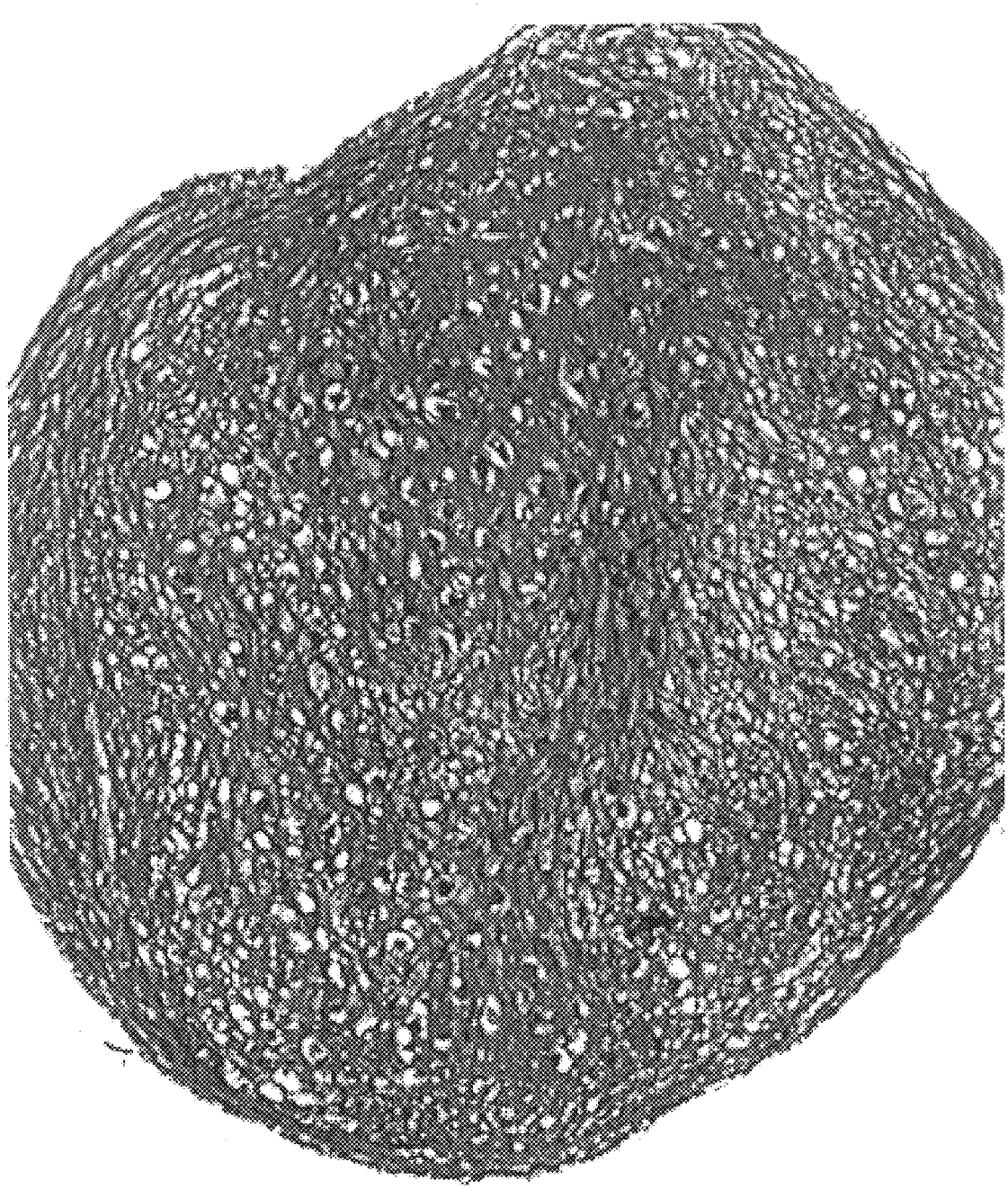
FIGS. 4A, 4B and 4C. Cells were grown under chondrogenic conditions in the absence of hyaluronic acid derivatives and stained with Toluidine blue after (FIG. 4A) 11, (FIG. 4B) 15 and (FIG. 4C) 21 days in culture.
Figure 4B:
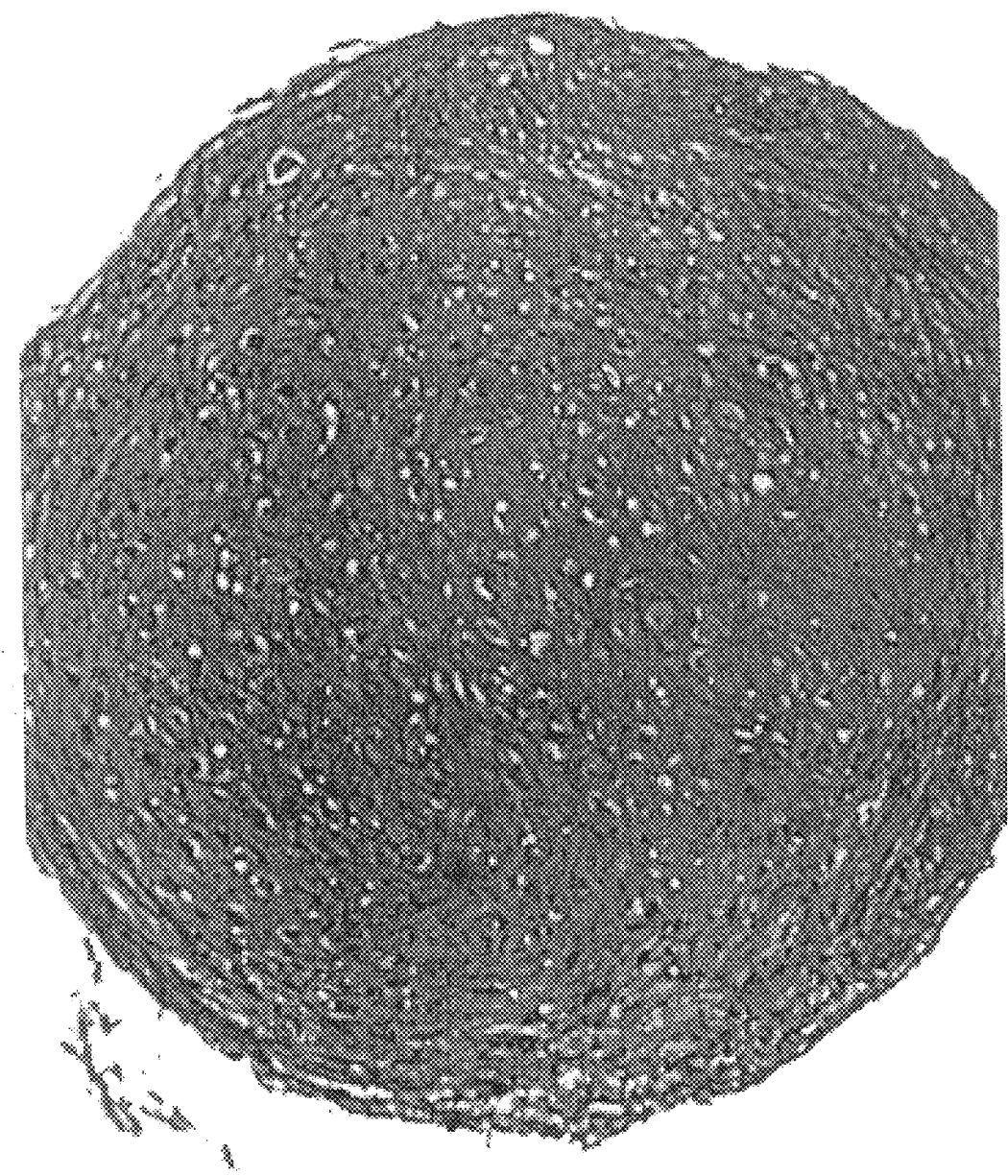
Figure 4C:
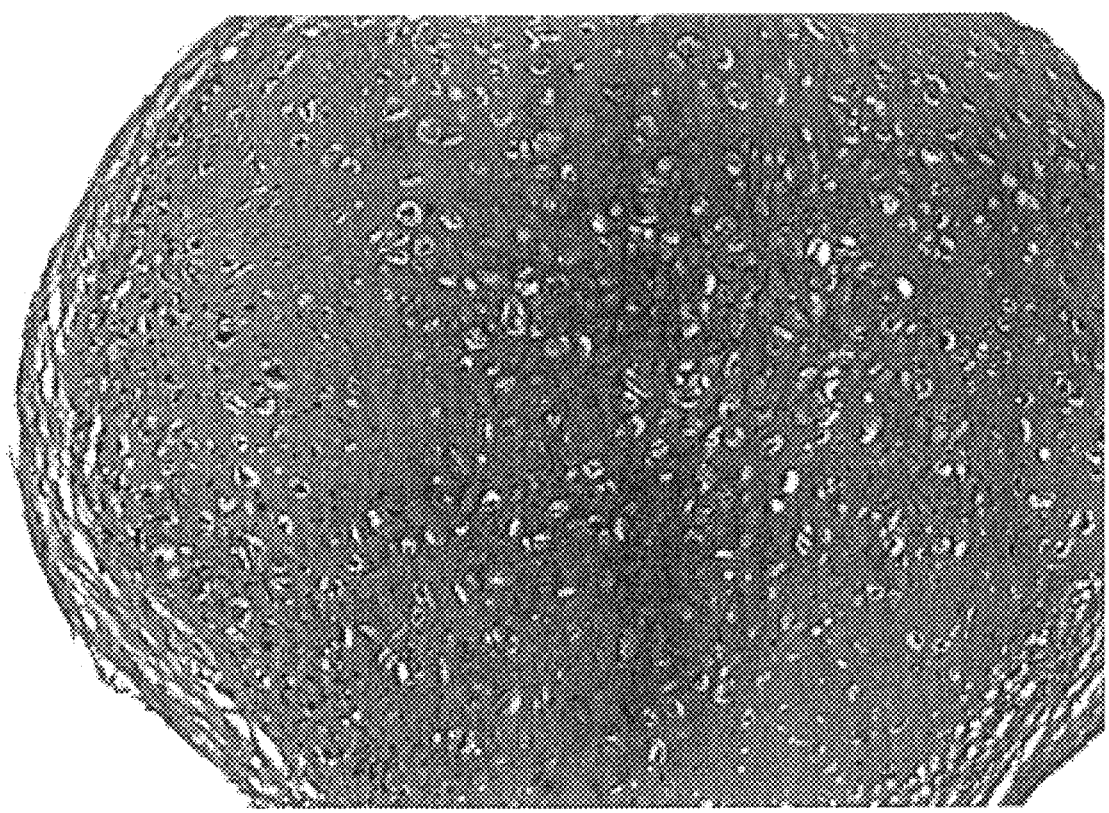

Control cultures: At 11 days in culture there was evidence of extracellular matrix deposition with metachromatic staining in the control cultures (FIG. 4A). There was a progressive increase at day 15 (FIG. 4B) and by 21 days in culture the pellet was completely. Toluidine blue positive with the exception of the cells in the peripheral region (FIG. 4C). These cells retained a looser fibroblastic appearance.

Figure 5A:
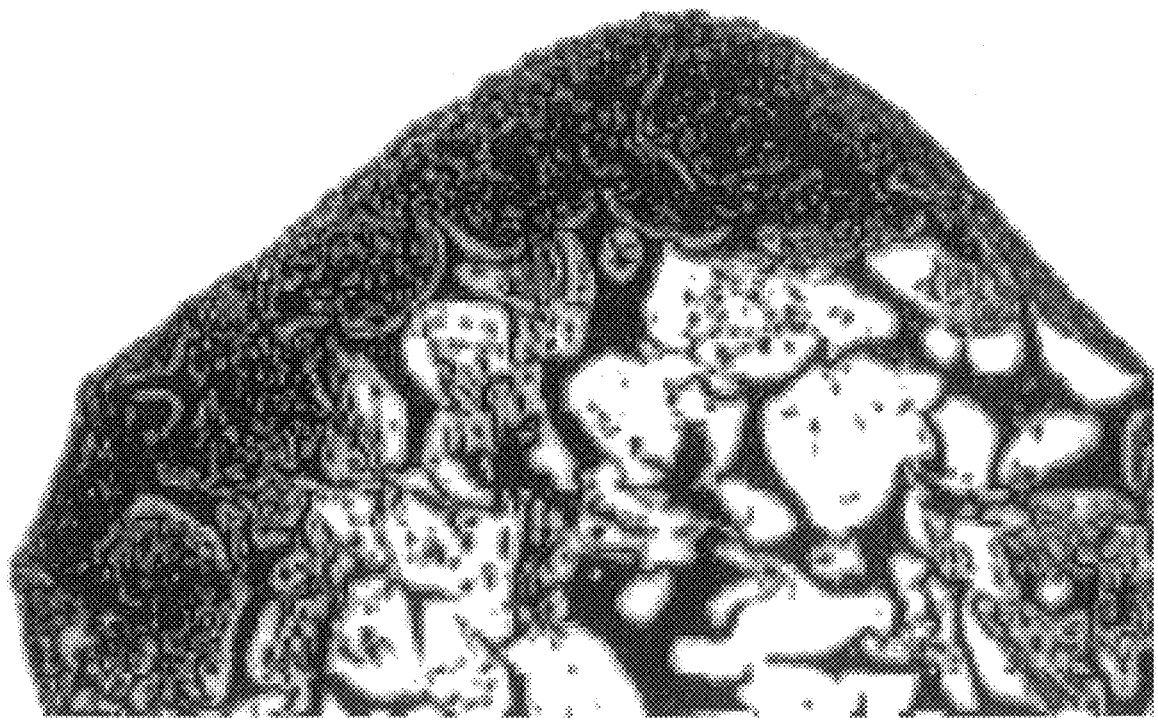
FIGS. 5A and 5B. Cells grown on HYAFF 11 sponge for (FIG. 5A) 11 and (FIG. 5B) 15 days and stained with Toluidine blue.
Figure 5B:
Figure 5C:
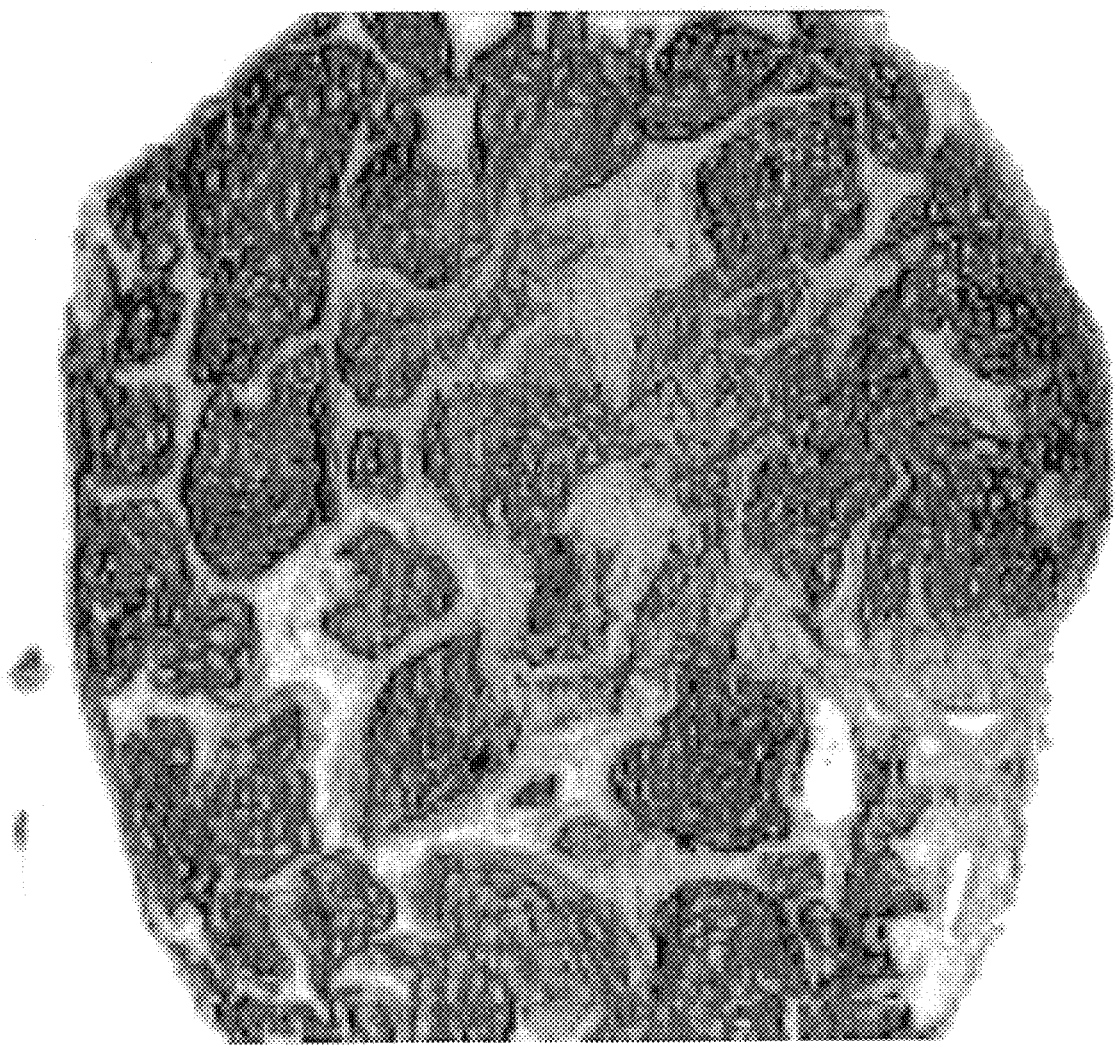
FIGS. 5C and 5D. Cells grown on HYAFF 11 sponge for 15 days and stained with an antibody specific for type II collagen. Original magnification 4× (FIG. 5A) and 10× (FIG. 5B).
Figure 5D:
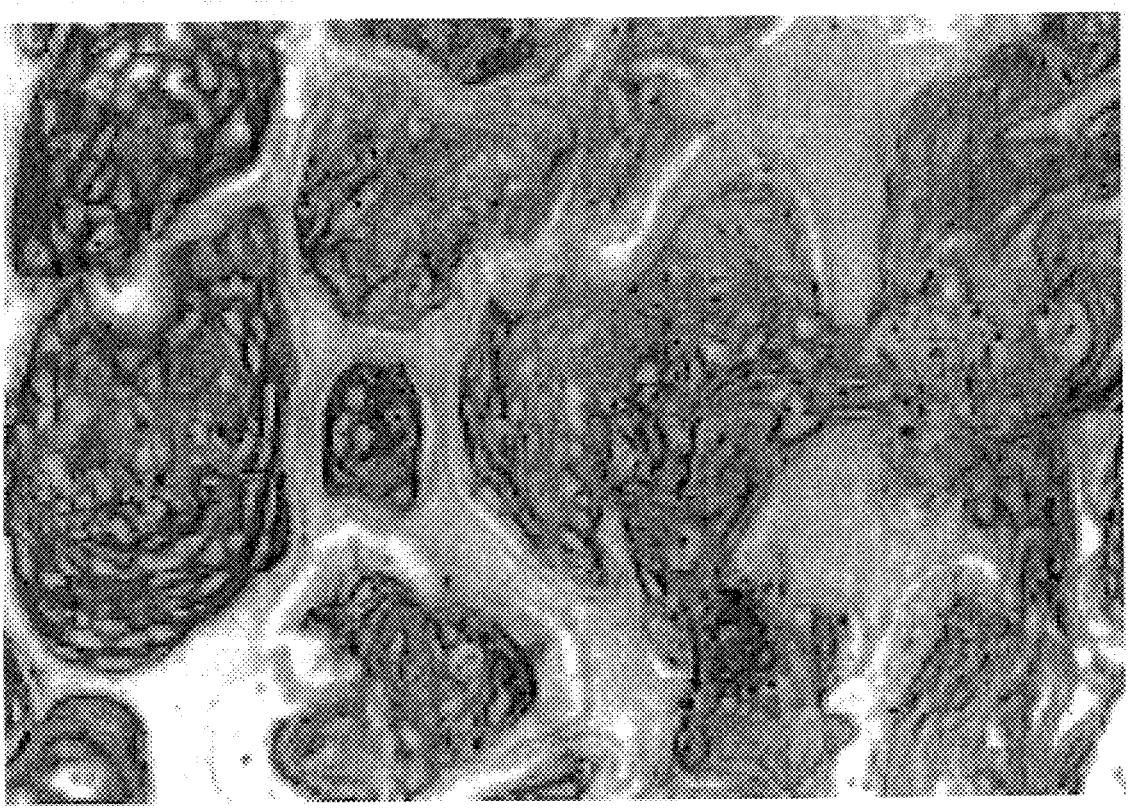

HYAFF II Sponge: Using the modified protocol described above in this Example, the loading density was much improved in these constructs compared to those described in Example 1. The sponge pores became impregnated with cells which, after 11 days in culture, (FIG. 5A) were strongly Toluidine blue positive in the peripheral pores. After 15 days in culture (FIG. 5B) the construct was filled throughout with cells which showed positive Toluidine blue staining. These cells stained intensely for collagen II as shown in FIGS. 5C and 5D.

Figure 6A:
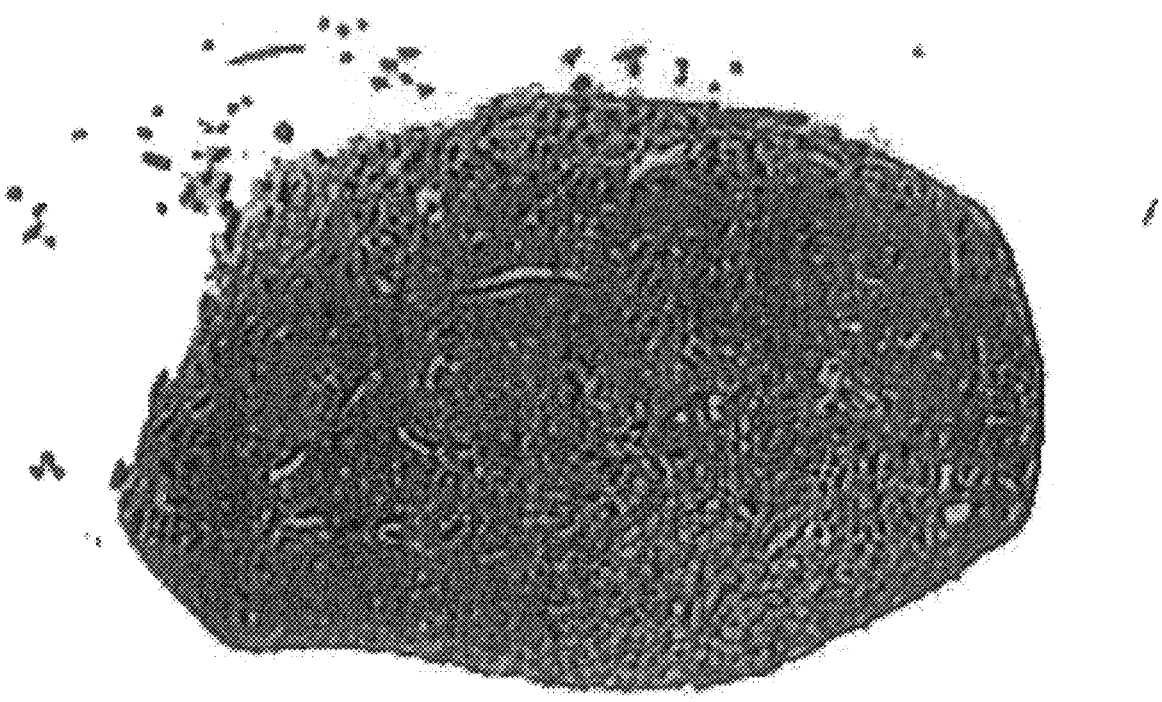
FIGS. 6A and 6B. MSCs were loaded onto HYAFF 11 non-woven fabric as described and grown for 15 days to form cultures that had a morphology similar to those seen in control cultures, but with a greater degree of chondrogenic differentiation, as seen by Toluidine blue staining at (FIG. 6A) 4× and (FIG. 6B) 10× original magnification.
Figure 6B:
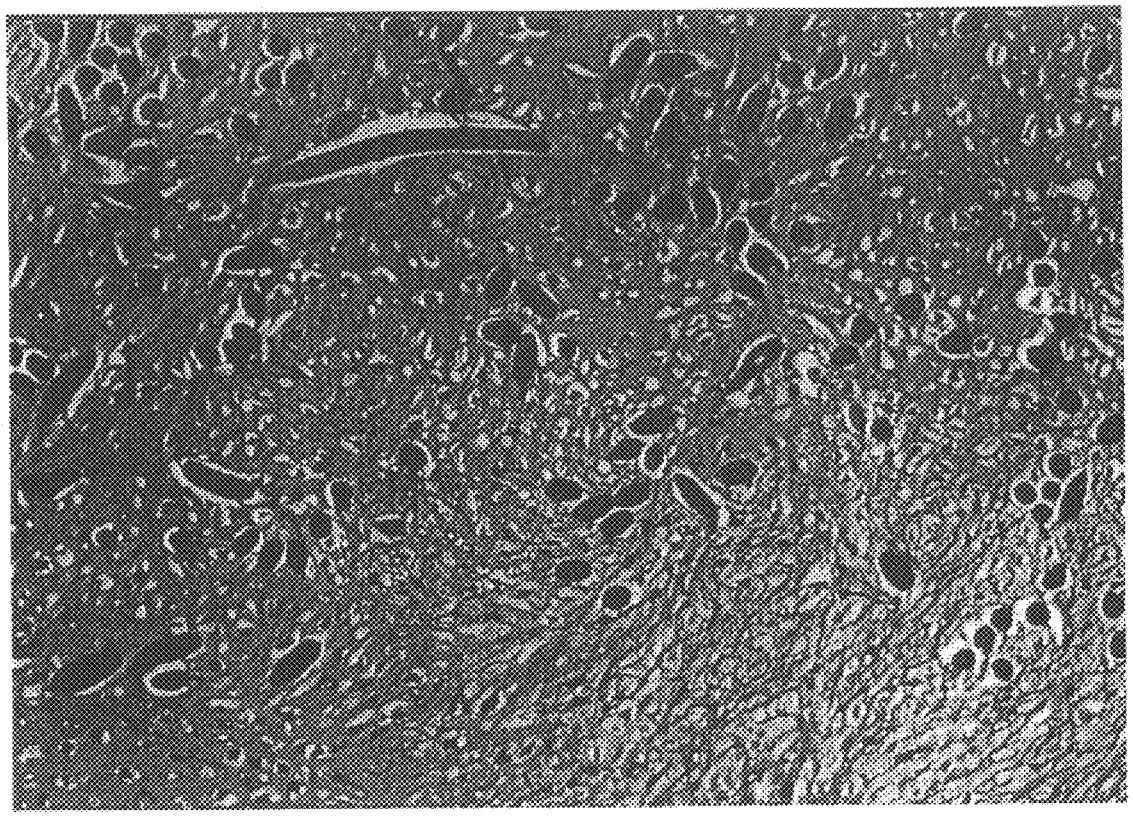
Figure 6C:
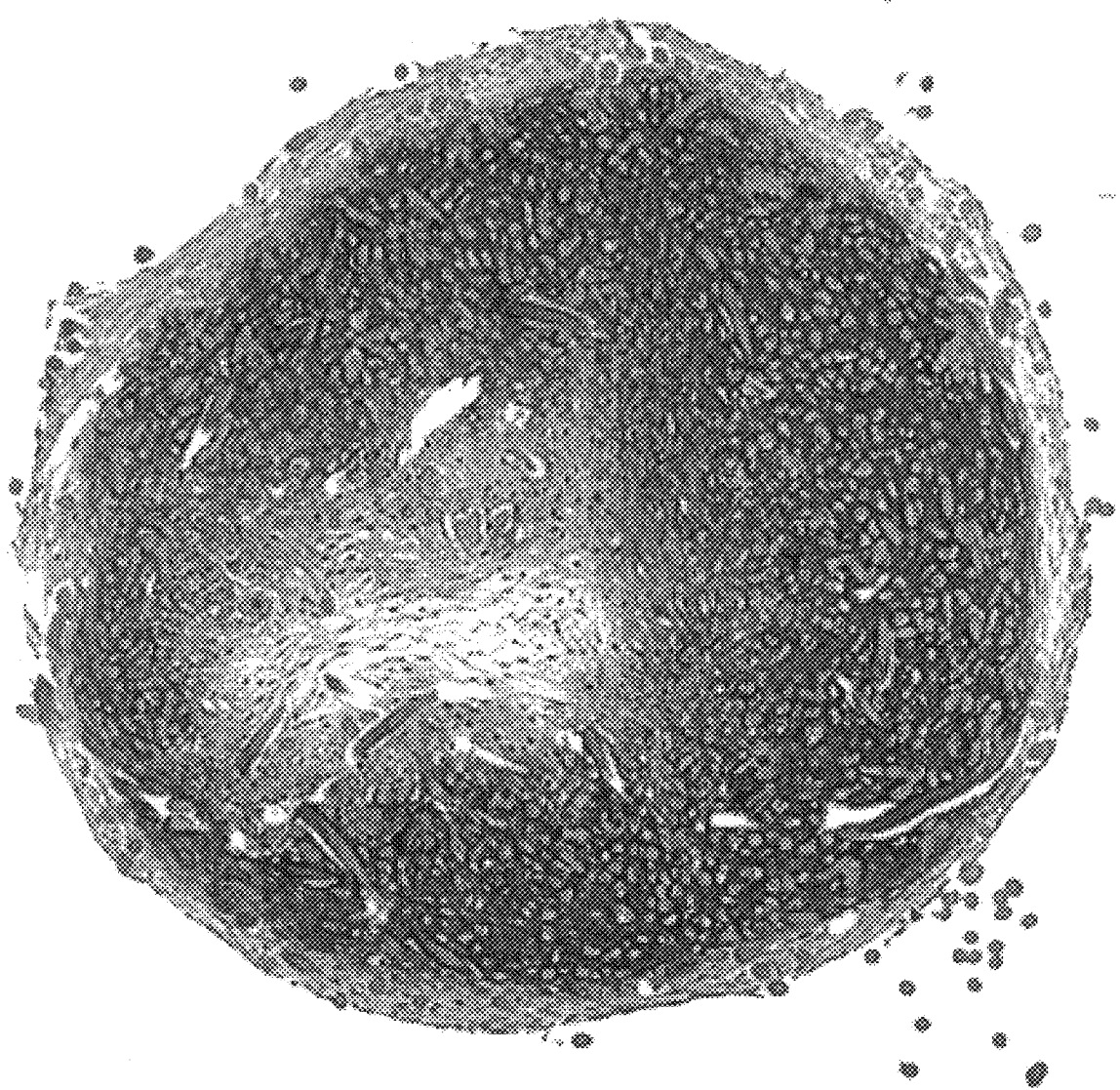
FIGS. 6C and 6D MSCs were loaded onto HYAFF 11 non-woven fabric and grown for 15 days to form cultures that showed strong reactivity with a collagen II specific antibody at (FIG. 6C) 4× and (FIG. 6D) 10× original magnification.
Figure 6D:
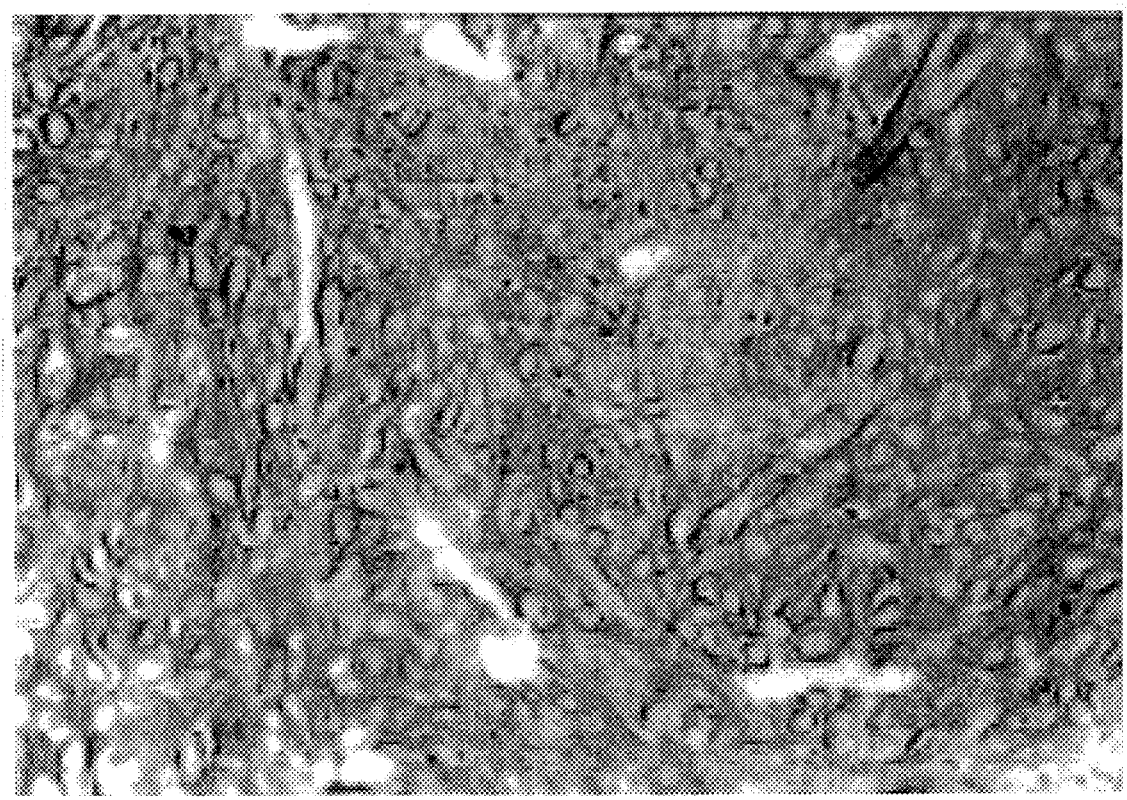

HYAFF 11 Fabric: MSCs loaded onto the fabric as described above in this Example grew to form cultures that had a morphology similar to those seen in control culture, but with a greater degree of chondrogenic differentiation, as seen by Toluidine blue staining (FIGS. 6A and 6B) and collagen II reactivity (FIGS. 6C and 6D).

ACP Gel: Cells were grown in the presence of ACP gel at concentrations of 0.25. 0.5 and 1.0%. There was a difference in the degree of chondrogenic differentiation, based on the level of metachromatic staining with Toluidine blue (FIGS. 7A and 7B). The highest level of metachromasia was seen with the 0.5% gel, suggesting that this may be the optimal concentration of chondrogenesis. At 0.25 and 15% there was little evidence of metachromasia.

When probed with an antibody for type II collagen (FIGS. 7C and 7D) only the culture in 0.5% gel showed reactivity.

Conclusions

HYAFF 11 materials in a variety of formats support or enhance the chondrogenic differentiation of human MSCs in such a way that the cells are stimulated to produce a proteoglycan-rich and type II collagen-rich extracellular matrix. This effect is more pronounced in those cells that are grown on HYAFF 11 compared to control cultures. These results provide several opportunities for designing MSC-HYAFF constructs for use in repair of chondrous and osseous lesions, in the repair of defects in tendon and ligament tissues, and for the repair of other connective tissue defects.

EXAMPLE 3

Support of In vitro Osteogenesis of Human Bone Marrow-derived MSCs

The objective of this series of experiments was to assess the osteogenic potential of human MSCs cultured on HYAFF 11 non-woven fabrics (H11-NWF).

Methods

The H11-NWF was cut into pieces roughly 5 mm×5 mm and placed individually into wells of a 6-well dish. Subsequently, 20 µl of a hMSC (passage-1) suspension at a concentration of $7.5 \times 10^6$ cell/ml were pipetted onto each of the samples, i.e. roughly $1.8 \times 10^{-5}$ cells/sample. The samples were incubated for two hours and then 2 ml of complete culture medium was added to each well. At the end of 24 hours of incubation, the medium was either replaced with fresh complete medium or complete medium augmented with osteogenic supplements (OS) namely 100 nM dexamethasone, 1 µM b-glycerophosphate and 50 µM ascorbic acid 2-phosphate. The medium was changed with the corresponding medium twice weekly. At the end of 6, 10 and 13 days of culture, the samples were harvested and cut into two pieces. One piece was used for biochemical assay to determine alkaline phosphatase activity and calcium deposition, and the other piece was used to obtain histological sections.

Results and Discussion

The data from the biochemical assay are shown in Table III.

TABLE III

Alkaline phosphatase activity and calcium deposition levels of hMSCS cultured in HYAFF-11 non-woven fabric in osteogenic and control conditions

| | Alkaline phosphatase (nmoles/min) | | Calcium deposition (µg/sample) | |
| --- | --- | --- | --- | --- |
| | Control | Osteogenic | Control | Osteogenic |
| Day 6 | 1.98 | 23.28 | 2.64 | 20.52 |
| Day 10 | 7.24 | 51.29 | 3.46 | 194.62 |
| Day 13 | 2.54 | 27.5 | 0.0 | 161.11 |

The control samples maintained basal levels of alkaline phosphatase through the duration of the experiment, and did not deposit any calcium. In contrast, the cells cultured in the osteogenic medium rapidly upregulated their alkaline phosphate activity and deposited calcium, indicating osteogenic differentiation of the cells. The calcium deposition levels in the OS treated cultures at the latter time points were over 50-fold higher that the corresponding controls.

Histological evaluation of the samples at the various time points showed that the hMSCs are distributed throughout the sample. There seemed to be more cells within the samples that were cultured in the osteogenic medium compared to those in the control medium, as is also seen in monolayer cultures. The cells in both cases seem to have laid down matrix filling in the pores of the implant. Photomicrographs of representative histological sections of a sample cultured in osteogenic medium are shown in FIG. 8.

Based on the above results, it is clear that H11-NWF supports osteogenic differentiation of MSCs and can serve as an appropriate matrix for MSCs delivery to achieve tissue regeneration.

EXAMPLE 4

In vivo Bone Formation in a Rat Femoral Gap Model

The HYAFF 11 material was subjected to in vivo screening in a rat femoral gap model as previously described and evaluated at 6 weeks post-implantation. Each of the materials was tested with and without marrow loading. In these series the ACP gel and the HYAFF 11 non-woven textile did not support marrow-mediated osteogenesis. However, in some of the HYAFF 11 sponge implants there were significant areas of bone regeneration. We also saw areas of cartilage blooms which indicated that this material would indeed find use in a formulation for articular cartilage repair. In the control experiments carried out with the addition of marrow the implants resulted in non-unions.

EXAMPLE 5
Temporomandibular Joint Disc Replacement in a Rabbit Model

The objective of this study was to formulate a MSC-loaded carrier which can serve as a TMJD replacement and be amenable to be sutured into place.

Methods

The strategy being used to construct this implant is to impregnate a HYAFF 11 non-woven fabric (H11-NWF) with a MSC-containing type-1 collagen gel (Pancogene, Gattafosse S. A., Lyons, France) and allowing it to set. The H11-NWF was cut to a size of 12 mm×4 mm and hydrated in serum-free DMEM. It was then folded onto itself and blotted to form a two-ply structure roughly 6 mm×4 mm in dimension. The blotted sample was then placed in a well of a 48-well dish. Separately, 125 µl of dialysed, chloroform-sterilized pancogene was mixed with a 125 µl of a $16 \times 10^6$/ml hMSC or IMSC (passage-1) suspension in serum-free DMEM.

Immediately, 200 µl of this collagen-cell suspension was added to the well containing the blotted HII-NWF and was allowed to percolate into the interior by aid of manual pressure on the sample. The sample was then allowed to set for one hour at 37° C. and then 1 ml of serum-free medium was added to the sample and the samples allowed to incubate for an additional 24–48 hours. At the end of the incubation period the samples were used for one of three purposes; 1) processed for histology; 2) placed into chondrogenic medium to determine if the MSCs could still be directed down the osteogenic lineage and; 3) implanted as an TMJD replacement bilaterally in a rabbit which had undergone a bilateral discectomy.

Results and Discussion

The samples retained their original shape and did not contract to any significant degree.

Preliminary histological observation revealed that the collagen gel had infiltrated throughout the samples and cells were uniformly distributed. The construct was tough enough and exhibited enough resistance to suture pull-out to allow it to be implanted in vivo as a TMJD replacement and be held in place by a suture. The animal experiment is ongoing and the implant seems so be well tolerated. The samples in the chondrogenic medium are at day 10 of culture and have maintained their original dimensions. The samples seem to be stiffer than at initiation to the chondrogenic culture however definitive data will not be available till the end of the culture on day 16.

The results and observations indicate that the H11-NWF/Collagen gel in combination with MSCs is an appropriate prostheses for TMJD.

EXAMPLE 6
Repair of the Medial Femoral Condyle

Bone marrow-derived cells were loaded into HA-based carriers at the end of primary culture. Briefly the cells were detached from the culture plates by trypsinization, counted and resuspended in the appropriate volume to make a suspension at the desired cell density. The HA-based materials, cut to the appropriate size, were soaked into the suspension and loaded in the implant applying negative pressure to the container to ensure a homogeneous distribution of cells throughout the volume of the implant. These composites were incubated for a minimum of two hours prior to implantation in the defects or subcutaneously in immunodepressed animals.

To evaluate the viability of the cells and the maintenance of their osteochondrogenic potential, the composites were implanted subcutaneously on the dorsal side of immunodepressed mice in pockets formed by blunt dissection. Mice were anaesthetised with an IP injection of pentobarbital at 45 mg/kg. When necessary, inhalant metofane was administered via nose cone in a biohazard hood. A small (1 cm) incision in the skin was made. Using blunt forceps, a small pouch was formed subcutaneously in the connective tissue between the skin and muscle. The implants were placed in the pouch. A metal staple was used to close the skin incision in the mice. Three and six weeks after the implantation duplicate mice were sacrificed by overdose of pentobarbital via I.P. and the implants were harvested and processed for histology.

In the cartilage repair studies, the composites were implanted in a cartilage defect created in the medial femoral condyle of the rabbit knee joint. Rabbits were anaesthetised with sodium penthotal given to effect (approximately 35 mg/kg body weight). The joint was approached via a medial parapatellar incision, reflecting the patella laterally. A defect 3 mm deep and 3 mm in diameter was formed in the weight-bearing region of the medial femoral condyle. The defect was flushed thoroughly with saline. The composite was implanted into the defect. The patella was returned to its anatomical site and the joint was closed with a 4-0 dexon. The overlying soft tissue and skin were closed routinely. Rabbits were sacrificed by overdose of pentobarbital via I.V. The knee joint was carefully dissected and the condyles cut and processed for histological analysis.

EXAMPLE 7
Meniscus Repair Studies

In the meniscus repair studies, composites prepared as described in Example 6 were sutured to the remaining lateral meniscus after an anterior medial meniscectomy in the rabbit knee joint. Rabbits were anaesthetised with sodium penthotal given to effect (approximately 35 mg/kg body weight). The joint was approached via a medial parapatellar incision, reflecting the patella laterally. The medial meniscus was cut approximally at its insertion with the caronal ligament and distally at the level of the collateral ligament. The composite was sutured to the coronal ligament, the synovial lining and the posterior half of the meniscus. The patella was returned to its anatomical site and the joint was closed with 4-0 suture. The overlying soft, tissue and skin were closed routinely. Rabbits were sacrificed by overdose of pentobarbital via I.V. The knee joint was carefully dissected and the meniscus harvested and processed for histological analysis.

EXAMPLE 8
Isolation and Culture of Stem Cells

About 5–10 ml of bone marrow is aspirated from the iliac crest or head of femur. The liquid, which also contains stromal bone fragments is placed in a 50 ml sterile tube and supplemented with 20–25 ml of Hank's saline solution at +4° C. The tube is centrifuged at approximately 1000 rpm for 5 minutes to eliminate the supernatant and the lipid layer, which are then aspirated. The excess of erythrocytes is eliminated by using Percoll or Ficoll type gradients, after which the fraction containing mesenchymal cells is removed and centrifuged at 1000 rpm for 5 minutes. The pellet is resuspended, removed and centrifuged in 5 ml of culture medium (a-MEM supplemented with foetal calf serum, 1% L-glutamine 200 mM, 1% penicillin/streptomycin 10,000 U/10,000 µg/ml) and seeded in Petri dishes with a diameter of 100 mm at a density of 50–100×106 nucleate cells/dish.

EXAMPLE 9

Transfer of Stem Cells in a Three Dimensional Matrix Consisting of HYAFF$^R$ 11 and HYAFF11 P75 and Differentiation of Stem Cells into Fibroblasts The cells are then left to incubate (37° C. pCO2 about 5%) for 72 hours, after which the medium is changed in order to remove any nonadhered cells. The mesenchymal cells remaining on the dish can be amplified by further passages (generally split ratio 1:3) and transferred to nonwoven tissue matrices of HYAFF$^R$ 11 and HYAFF$^R$ 11p75, adding growth factor bFGF (1 ng/ml) to the culture medium. Some time later (1–2 weeks) the cells inside the biomaterial take on a fibroblast appearance and express phenotypes typical of fibroblasts with the production of typical molecules of the connective matrix (collagen type I, II, III, IV, fibronectin, laminin).

EXAMPLE 10

Preparation of
dermis a containing;
  fibroblasts from bone marrow stem cells
  three dimensional matrix consisting of nonwoven HYAFF$^R$ 11
dermis a (control) containing
  fibroblasts coming from human dermis
  three dimensional matrix consisting of nonwoven HYAFF$^R$ 11
dermis β containing:
  fibroblasts from bone marrow stem cells
  three dimensional matrix consisting of nonwoven HYAFF$^R$ 11 p75
dermis β (control) containing:
  fibroblasts coming from human dermis
  three dimensional matrix consisting of nonwoven HYAFF$^R$ 11 p75

Pieces of tissue (1.5×1.5 cm) comprised of both HYAFF$^R$ 11p75 and HYAFFR 11, are separately attached onto culture dishes by means of a fibrin clot. Human fibroblasts obtained from skin explants or from mesenchymal stem cells from bone marrow isolated and grown as described in Example 1 are separately seeded on the biomaterial at a density of $10^4$ cells×cm$^2$ in 0.2 ml of medium, soaking the biomaterial slowly. After about 30 minutes, DMEM culture medium complete with 10% FCS and 50 µg/ml of I-ascorbic acid are added and the dishes are incubated at 37° C.

The medium is changed every 48 hours and the cultures are observed by phase-contrast microscope.

The pieces of biomaterial made of HYAFF$^R$ 11 p75 can be cultured only for 7 days and since it has been seen that, in the case of fibroblast cultures on HYAFF-11p75, the biomaterial begins to dissolve in the medium after 7 days. HYAFF-11, on the other hand, can be kept in culture for much longer (about 6 weeks). In this case, the pieces of HYAFF-11 are incubated with the cells for periods of 7, 14 and 21 days.

At the end of the culture period, the matrices of hyaluronic acid benzylester HYAFF$^R$ 11 p75 and HYAFF$^R$ 11, containing the fibroblasts from stem cells and the corresponding ones containing fibroblasts from human skin are detached from the dish without using lithic enzymes and divided into two parts.

One is fixed in formalin for routine histological tests and the other is frozen in liquid nitrogen and stored for subsequent immunohistochemical investigation.

The pieces fixed in formalin are stained with hematoxylin/eosine or by van Gieson's method, while the frozen material is stained immunohistochemically with mono- or polyclonal antibodies to show the presence of fibronectin, collagen I, II and IV, laminin.

Results of Histological Staining

Hematoxylin/eosin

Elongated cells with typical fibroblast morphology are observed both in HYAFF$^R$ 11p75 and HYAFF$^R$ 11 biomaterials. From a morphological point of view, the fibroblasts obtained from dermis and those obtained from bone marrow mesenchymal cells are similar in appearance. In the case of HYAFF$^R$ 11, the fibres of the biomaterial are well preserved, while the HYAFF$^R$ 11p75 fibres show signs of disintegration.

Analysis of the biomaterial shows the presence of a delicate mesh of fine fibrils which turn pale pinkish red on staining with the Van Gieson method, confirming that they are collagen fibrils neosynthesized by the fibroblasts.

Immunohistochemical Characterisation

The following antibodies were used to reveal the most representative molecules in the extracellular matrix:
1) human I anticollagen monoclonal antibodies
2) human III anticollagen monoclonal antibodies
3) human IV anticollagen monoclonal antibodies
4) human antifibronectin monoclonal antibodies
5) human antilaminin monoclonal antibodies The extracellular matrix deposited by the fibroblasts, both of dermal and bone marrow mesenchymal derivation, proved to be positive to the above immunoreactions. In particular, a notable fibrillar collagen (I and III) component was observed, as well as collagen IV. The typical adhesive molecules, fibronectin and laminin, which are characteristic of dermal tissue, are clearly expressed by these fibroblast cells, showing that a complete extracellular scaffold can be constituted within the matrices used by the Applicant.

EXAMPLE 11

Cryopreservation of dermis and dermis are prepared as described in Example 10 in order to demonstrate the possibility of preserving the artificial dermis obtained from stem cell culture in cold storage, the pieces of biomaterial containing the cells were frozen in the presence of a cold storage agent (dimethylsulfoxide, DMSO). The cultures were removed and placed in capsules containing DMEM, FCS and 10% DMSO, cooled to 4° C. and then frozen to −80° C. 5 minutes later.

One week later, the pieces of HYAFF$^R$ 11p75 were thawed from frozen and rapidly heated to 37° C. washed several times with DMEM with 10% FCS in order to eliminate the DMSO. They were left in an incubator for 24 hours, after which the cultures were transferred onto new pieces of HYAFF$^R$ 11 p75 biomaterial of the same dimensions, which had been attached to culture dishes. This step is necessary to provide the cells with a new support, as the original nonwoven tissue starts to dissolve in the medium after 7 days.

The pieces of HYAFF$^R$ 11, on the other hand, were reused for culture after freezing in the conditions described above. All the thawed biomaterials were cultured for 7 days and then analysed as described in example 1. These new findings are similar to those described in example 1 and the tests performed with trypan blue staining show that the cells present in the HYAFF$^R$ 11 matrix are still viable after thawing.

FIGS. 9–13/A–B show histological photographs of the HYAFF^R 11 nonwoven biomaterial wherein human fibroblasts from bone marrow and dermis have been seeded. Each figure describes the relative immunolocalization of collagen I, III, IV, fibronectin and laminin. The various biomaterials made of HYAFF^R 11 and HYAFF^R 11 p75 (gauzes, sponges, membranes) do not differ in any substantial way one from the other as far as fibroblast growth and the deposit of extracellular matrix is concerned.

What is claimed is:

1. A biological material for the repair of connective tissue defects comprising:
   a) a cell preparation enriched in mesenchymal stem cells which is able to differentiate into more than one connective tissue cell line in the presence of a mesenchymal specific differentiation agent for said connective tissue cell line;
   b) a three dimensional matrix comprising a hyaluronic acid derivative is selected from the group consisting of:
      a partial or complete ester of hyaluronic acid with an aliphatic, aromatic or araliphatic alcohol, and
      a crosslinked hyaluronic acid derivative.

2. The biological material according to claim 1 wherein (a) is a bone marrow, peripheral blood or cord blood isolate or a mesenchymal tissue extract enriched as to the proportions of mesenchymal stem cells therein.

3. The biological material according to claim 1 wherein (a) is an isolated homogenous population of mesenchymal stem cells able to differentiate into more than one connective tissue type.

4. The biological material according to claim 3 wherein said isolated homogeneous population of mesenchymal stem cells consists of mesenchymal stem cells free from differentiated stem cells and/or hematopoietic cells.

5. The biological material according to claim 3 wherein said isolated homogenous population of mesenchymal stem cells is an efficient culture of mesenchymal stem cells partially or completely differentiated into a specific connective tissue cellular lineage, optionally containing hematopoietic cells.

6. The biological material according to claim 1, wherein the three-dimensional matrix in the biological material is in the form of gel, woven, non-woven tissue or fabric, sponges, guide channel, gauzes, microspheres and granules.

7. The biological material according to claim 6, wherein said three dimensional matrix further comprises hyaluronic acid as such and/or a biocompatible material.

8. The biological material according to claim 6, wherein said three-dimensional matrix is formed by fibrous webs of a hyaluronic acid derivative interwoven with fibrous webs of a bioresorbable material other than a hyaluronic acid derivative.

9. The biological material according to claim 1 wherein said three-dimensional matrix consists of at least one of said hyaluronic acid derivatives.

10. The biological material according to 1 wherein said hyaluronic acid derivative is selected from the group consisting of:
    a partial or complete ester of hyaluronic acid with an aliphatic, aromatic or araliphatic alcohol, and
    a crosslinked hyaluronic acid derivative.

11. The biological material according to claim 10 wherein said total or partial hyaluronic acid esters are the benzyl esters.

12. The biological material according to claim 8, wherein said differentiation inductive agent is selected from the group consisting of osteogenic, chondrogenic, tendonogenic, ligamentogenic, myogenic, adipogenic, dermagenic, marrow-stromagenic, differentiation inductive agent.

13. A composition comprising the biological material according to claim 1 in combination with pharmaceutically acceptable excipients and/or diluents possibly associated with therapeutically active ingredients.

14. An implant consisting essentially of the biological material according to claim 1.

15. A therapeutic method for de novo formation of connective tissue in vivo by introducing into a site for de nova connective tissue formation in an individual in need thereof a therapeutically effective amount of the composition according to claim 13.

16. A surgical method for de novo formation of connective tissue in viva by introducing into a site for de novo connective tissue formation in an individual in need thereof the implant according to claim 14.

* * * * *